(12) United States Patent
Ma et al.

(10) Patent No.: US 11,629,160 B2
(45) Date of Patent: Apr. 18, 2023

(54) CORROLE-BASED FRAMEWORKS AND METHODS OF USE THEREOF

(71) Applicant: University of South Florida, Tampa, FL (US)

(72) Inventors: Shengqian Ma, Tampa, FL (US); Yanming Zhao, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 17/636,717

(22) PCT Filed: Aug. 20, 2020

(86) PCT No.: PCT/US2020/047112
§ 371 (c)(1),
(2) Date: Feb. 18, 2022

(87) PCT Pub. No.: WO2021/035010
PCT Pub. Date: Feb. 25, 2021

(65) Prior Publication Data
US 2022/0267361 A1    Aug. 25, 2022

Related U.S. Application Data

(60) Provisional application No. 62/889,077, filed on Aug. 20, 2019.

(51) Int. Cl.
*C07F 15/02*     (2006.01)
*B01J 31/16*     (2006.01)

(52) U.S. Cl.
CPC ......... *C07F 15/025* (2013.01); *B01J 31/1691* (2013.01)

(58) Field of Classification Search
None
See application file for complete search history.

(56) References Cited

U.S. PATENT DOCUMENTS

2017/0231903 A1   8/2017   Lin et al.
2018/0147284 A1   5/2018   Orellana-Tavra et al.
2018/0274013 A1   9/2018   Zhang et al.

OTHER PUBLICATIONS

Stergiannakos T. et al., "Hydrogen Storage in Novel Li-Doped Corrole Metal-Organic Frameworks", The Journal of Physical Chemistry C, 2012, vol. 116, issue 15, pp. 8359-8363.
Zhao Y. et al., "Robust Corrole-Based Metal-Organic Frameworks with Rare 9-Connected Zr/Hf-Oxo Clusters", Journal of the American Chemical Society, Aug. 21, 2019 (Aug. 21, 2019), vol. 141, issue 36, pp. 14443-14450.

*Primary Examiner* — Joseph R Kosack
(74) *Attorney, Agent, or Firm* — Quarles & Brady LLP

(57) ABSTRACT

Described herein are corrole-based frameworks and methods for making the same. The corrole-based frameworks have unique structural and physical properties, which lends them to be versatile in a number of different applications and uses such as in gas storage/separation, proton conduction, biomedicine, sensing, and catalysis. In one aspect, the corrole-based frameworks are organic frameworks. In other aspects, the corrole-based frameworks are metal-organic frameworks.

15 Claims, 9 Drawing Sheets

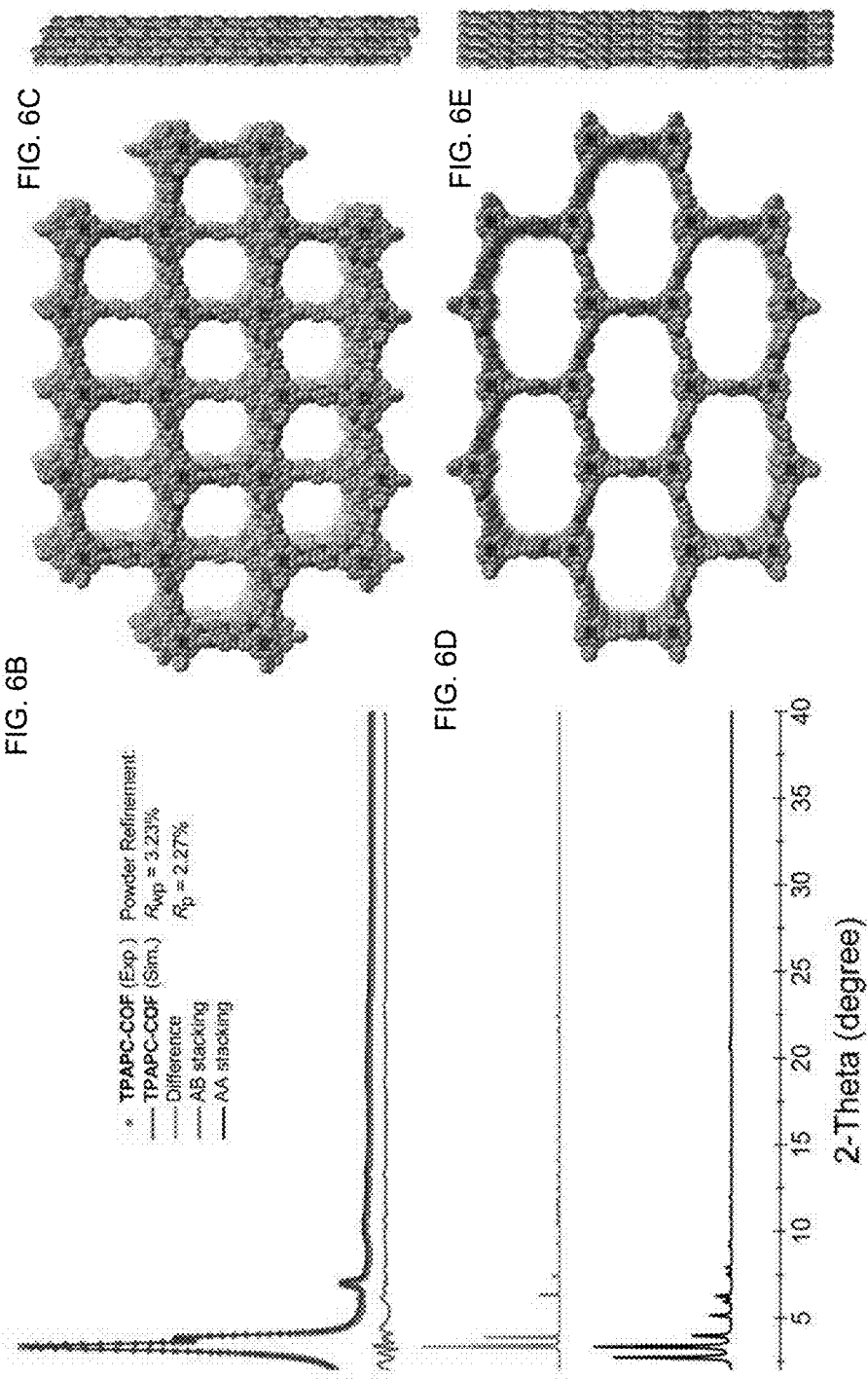

FIG. 7A
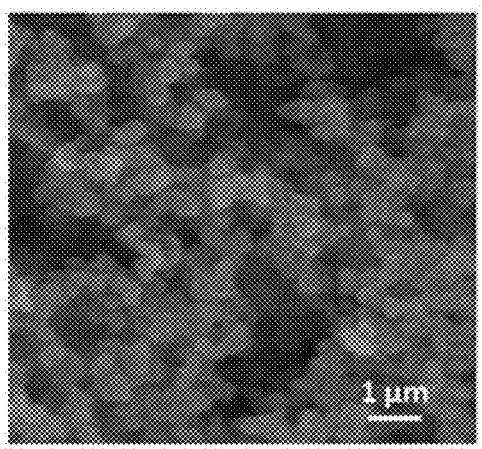
FIG. 7B
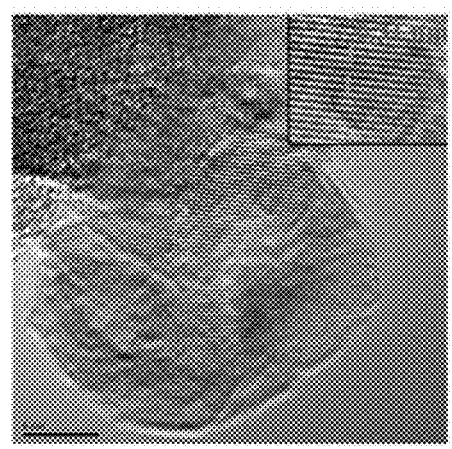
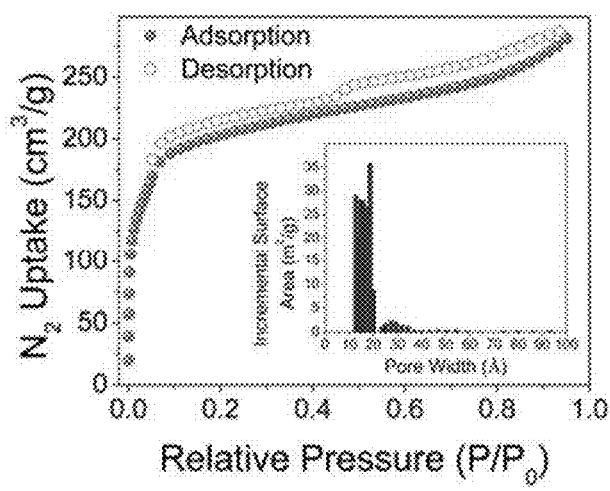
FIG. 7C
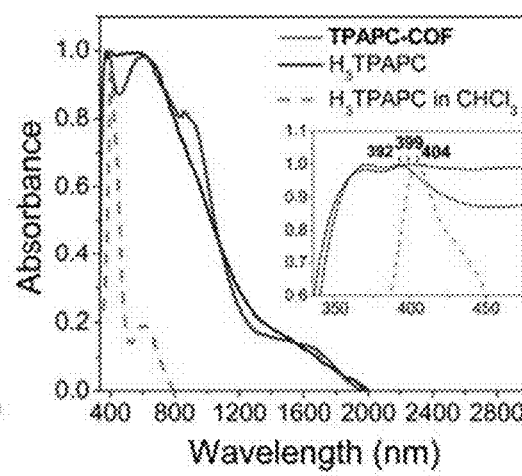
FIG. 7D

FIG. 8A
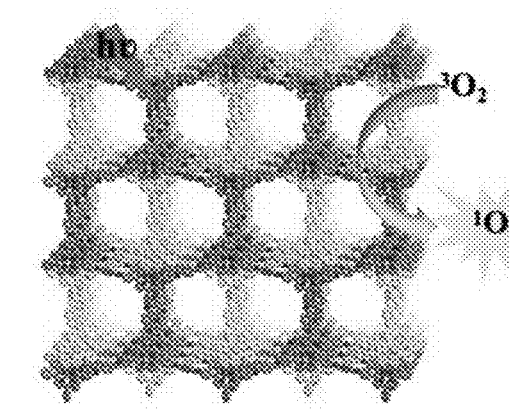
FIG. 8B
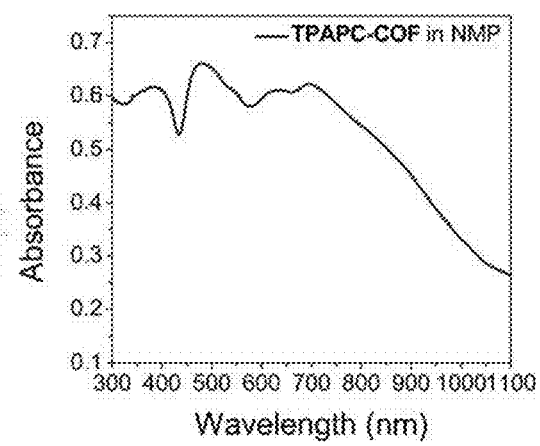
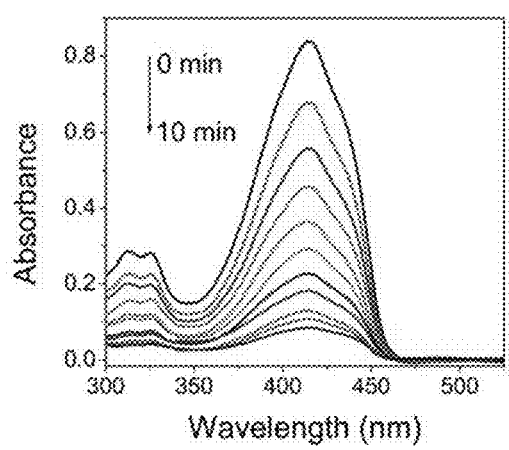
FIG. 8C
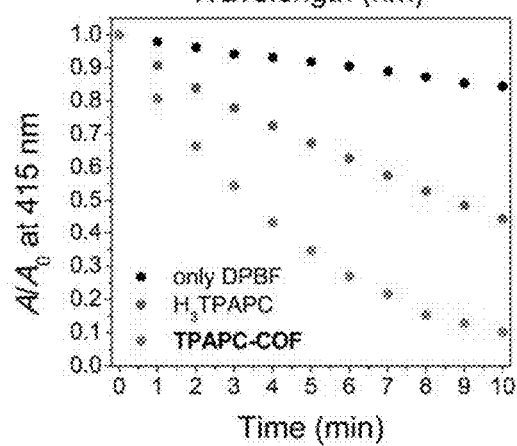
FIG. 8D

FIG. 9A
FIG. 9B
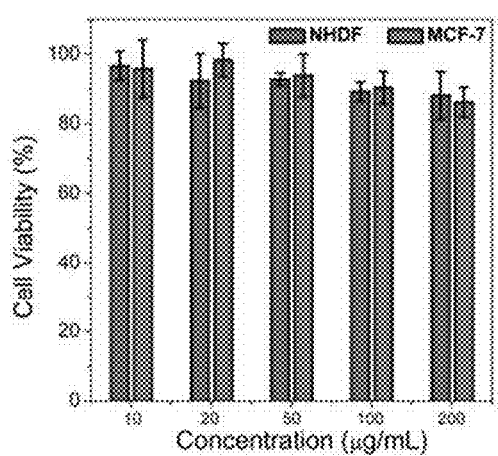
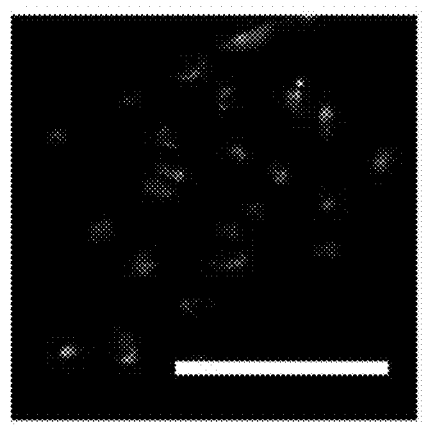
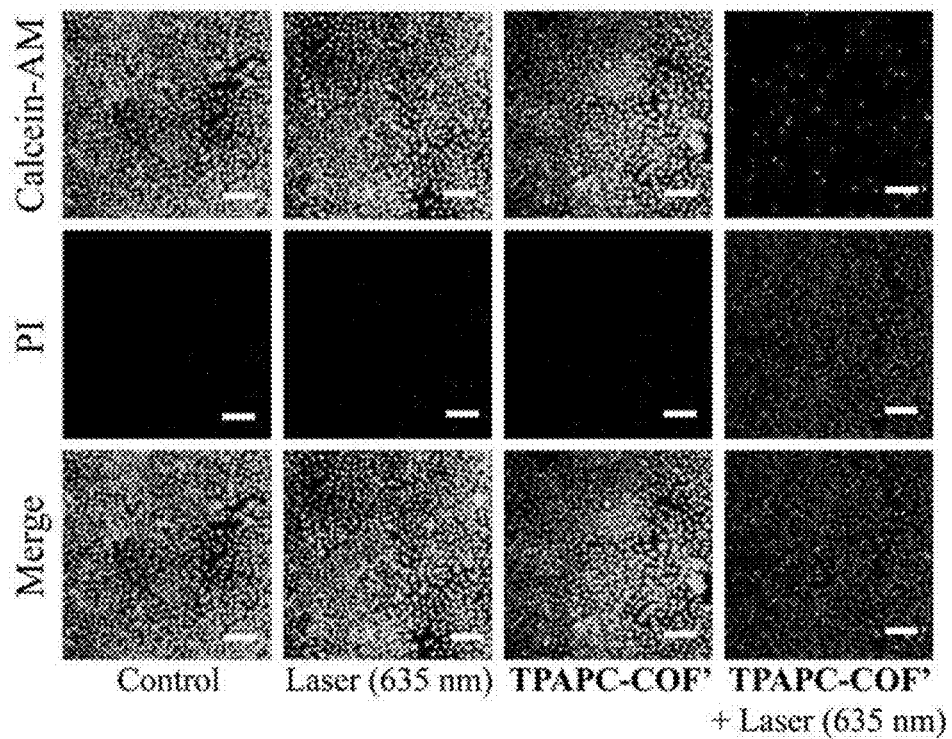
FIG. 9C

CORROLE-BASED FRAMEWORKS AND METHODS OF USE THEREOF

CROSS REFERENCE TO RELATED APPLICATIONS

This application represents the U.S. national stage entry of International Patent Application Serial No. PCT/US2020/047112, filed Aug. 20, 2020, which claims priority to U.S. provisional patent application Ser. No. 62/889,077 filed on Aug. 20, 2019, the contents of each are hereby incorporated by reference in their entirety.

BACKGROUND

Coinciding with the development of synthetic methodologies for the preparation of free-base corroles, the corrole chemistry has witnessed an immense boost in the last two decades, ranging from syntheses to properties to applications. Specially, corroles as the 18π electron tetrapyrrolic macrocycles from the porphyrinoid family, display the unique structure with a direct pyrrole-pyrrole link containing a smaller cavity and three protons in the inner core of the ring, which come with attractively distinctive spectroscopic and photophysical properties as well as the peculiar coordination chemistry and chemical reactivity. These prominent features make such a burgeoning class of macrocyclic compounds show great potential in diverse fields including catalysis, energy conversion, chemical sensors, optoelectronics, and biological and medical applications. Nevertheless, studies that directly and systematically introduce these motifs into porous crystalline framework materials for targeting further functionalizations are lacking. There still remains an outstanding synthetic challenge to fine-tune and control the growth of networks incorporating corrole derivatives.

SUMMARY

Described herein are corrole-based frameworks. The corrole-based frameworks have unique structural and physical properties, which lends them to be versatile in a number of different applications and uses. In one aspect, the corrole-based frameworks are organic frameworks. In other aspects, the corrole-based frameworks are metal-organic frameworks.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below:

(FIG. 1A) tricarboxylic corrolic linker, H$_3$TCPC; (FIG. 1B) D$_{3d}$-symmetric 9-connected Zr$_6$ cluster; (FIG. 1C) schematic representation of the (3,9)-connected net for Corrole-MOF-1 framework; (FIG. 1F, FIG. 1E) view of Corrole-MOF-1 respectively along the c and a axes with uniform 1D open channels; (FIG. 1F, FIG. 1G) magnified parts in the structure displaying the connectivity between corrole ligands and Zr$_6$ clusters (Zr, C, O, N atoms are shown in aqua, black, red, blue spheres, respectively, with H atoms are omitted for clarity).

FIGS. 6A-6E show (FIG. 6A) PXRD patterns of TPAPC-COF with the experimental in red, Pawley refined in blue, difference between experimental and refined data in olive, and simulated AB and AA stacking respectively in orange and black; (FIG. 6B, FIG. 6C) space-filling models of the TPAPC-COF in AB stacking from top and side views respectively; and (FIG. 6D, FIG. 6E) AA stacking from top and side views respectively.

FIGS. 7A-7D show (FIG. 7A) SEM image of TPAPC-COF; (FIG. 7B) HRTEM images of TPAPC-COF (inset shows the lattice distance); (FIG. 7C) N$_2$ sorption isotherms of TPAPC-COF at 77 K (inset shows the pore size distribution); (FIG. 7B) optical absorption spectra of the TPAPC-COF and monomer H$_3$TPAPC measured in diffuse reflectance and H$_3$TPAPC measured in diluted CHCl$_3$ solution (inset shows enlarged region from λ=335 to 475 nm).

FIGS. 8A-8D show (FIG. 8A) schematic diagram of TPAPC-COF generating singlet oxygen; (FIG. 8B) absorption spectrum of TPAPC-COF dispersed in N-methylpyrrolidone (50 µg/ml); (FIG. 8C) UV-vis spectra of DPBF solution with TPAPC-COF under a 635 nm laser (0.18 W/cm$^{-2}$) irradiation for 10 min; (FIG. 8D) The quantification of the $^1O_2$ generation ability of DPBF blank, H$_3$TPAPC and TPAPC-COF.

FIGS. 9A-9C show (FIG. 9A) the viability of NHDF and MCF-7 cells treated with different concentrations of TPAPC-COF' (10, 20, 50, 100 and 200 µg/ml), (FIG. 9B) CLSM of $^1O_2$ generation in MCF-7 cells treated with TPAPC-COF' upon irradiation at 635 nm for 5 min; (FIG. 9C) CLSM of MCF-7 cells after different treatments: (A) Control, (B) Laser (635 nm), (C) TPAPC-COF', and (D) TPAPC-COF'+Laser (635 nm). All of the scale bars are 200 µm.

DETAILED DESCRIPTION

Figures 1A, 1B, 1C, 1D, 1E, 1F, 1G:
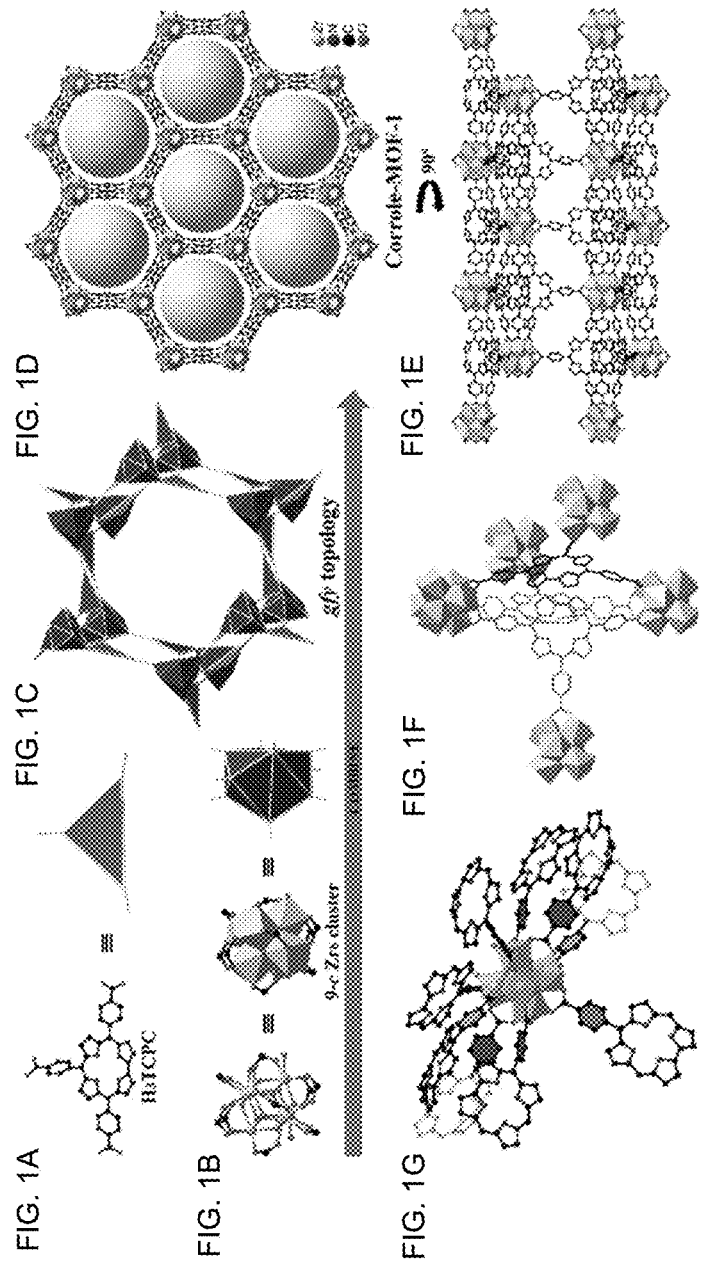
FIGS. 1A-1G show the crystal structure, structural components and underlying network topology of Corrole-MOF-1 after removal of disorder.

Before the present materials, articles and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a solvent" includes mixtures of two or more solvents and the like.

"Optional" or "optionally" means that the subsequently described event or circumstance can or cannot occur, and that the description includes instances where the event or circumstance occurs and instances where it does not. For example, the compositions described herein may optionally contain a hydrophilic compound, where the hydrophilic compound may or may not be present.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, the term "about" is used to provide flexibility to a numerical range endpoint by providing that a given numerical value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

As used herein, the term "admixing" is defined as mixing two or more components together so that there is no chemical reaction or physical interaction. The term "admixing" also includes the chemical reaction or physical interaction between the two or more components.

As used herein, "alkyl group" is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. In one aspect, the alkyl group is a branched or unbranched $C_1$ to $C_{10}$ group.

As used herein, "aryl group" is any carbon-based aromatic group including, but not limited to, benzene, naphthalene, etc. The term "aryl group" also includes "heteroaryl group," which is defined as an aryl group that has at least one heteroatom incorporated within the ring of the aromatic ring. Examples of heteroatoms include, but are not limited to, nitrogen, oxygen, sulfur, and phosphorus. In one aspect, the heteroaryl group is imidazole. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

As used herein, "aralkyl group" is an alkyl group as defined herein substituted with one or more aryl groups as defined herein. An example of an aralkyl group is a benzyl group.

As used herein, "carboxyl group" has the formula —$CO_2R$, where R is hydrogen, an alkyl group, aryl group, or aralkyl group as defined herein. The carboxyl group can also exist as a salt.

As used herein, "alkoxy group" has the formula RO—, where R is an alkyl group, aryl group, or aralkyl group as defined herein.

The term "transition metal" as defined herein includes the elements of groups 3 to 11 in the periodic table as well as the lanthanide and actinide elements The term "solid tumor" as defined herein is an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas.

The term "subject" as defined herein is any organism in need of cancer treatment and/or prevention. In one aspect, the subject is a mammal including, but not limited to, humans, domesticated animals (e.g., dogs, cats, horses), livestock (e.g., cows, pigs), and wild animals.

The term "treat" as used herein is defined as maintaining or reducing the symptoms of a pre-existing condition. For example, the frameworks described herein are used to treat cancer.

The term "prevent" as used herein is defined as eliminating or reducing the likelihood of occurrence of one or more symptoms of a disease or disorder. For example, the frameworks described herein can be used to prevent the regrowth of tumor cells or reduce the rate of regrowth of tumor cells.

The term "inhibit" as used herein is the ability of the frameworks described herein to completely eliminate an activity or reduce the activity when compared to the same activity in the absence of the framework. For example, the frameworks described herein can be used to inhibit the growth and/or spread of cancer in the body of a subject.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, from about 1—about 3, from 1 to about 3, from about 1 to 3, etc., as well as 1, 2, 3, 4, and 5, individually. The same principle applies to ranges reciting only one numerical value as a minimum or maximum. The ranges should be interpreted as including endpoints (e.g., when a range of "from about 1 to 3" is recited, the range includes both of the endpoints 1 and 3 as well as the values in between). Furthermore, such an interpretation should apply regardless of the breadth or range of the characters being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed, that while specific reference to each various individual combination and permutation of these compounds may not be explicitly disclosed, each is specifically contemplated and described herein. For example, if a transition metal is disclosed and discussed, and a number of different corroles are discussed, each and every combination of transition metal and corrole that is possible is specifically contemplated unless specifically indicated to the contrary. For example, if a class of transition metals A, B, and C are disclosed, as well as a class of corroles D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such composition is specifically contemplated and should be considered disclosed.

Metal-Organic Frameworks

In one aspect, described herein are metal-organic frameworks (referred to herein as MOFs). The metal-organic frameworks described herein are three dimensional structures composed of a plurality of pores and channels. The metal-organic frameworks are composed of a plurality of structural units arranged in a specific pattern.

In one aspect, the metal-organic framework comprises a structural unit comprising the formula I $$M_6(\mu_3\text{—O})_4(\mu_3\text{—OH})_4(OH)_3(H_2O)_3(TAC)_9 \quad \text{I}$$

wherein M is a transition metal, and
TAC is a 5,10,15-tris(phenyl)corrole with an anionic group on each phenyl ring of the corrole.

The synthesis and structure of TAC is provided below, where A denotes the anionic group:

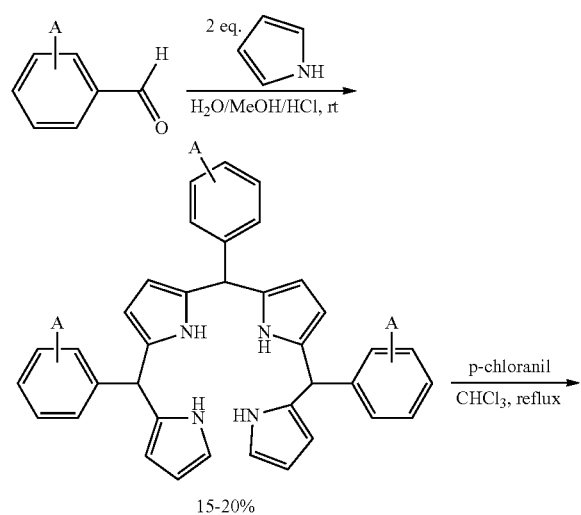

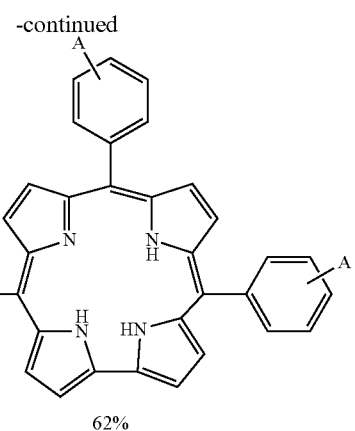

62%

TAC possesses three phenyl groups, where each phenyl group includes one or more anionic groups. The anionic group(s) can be positioned at the ortho, meta, and/or para positions of each phenyl group. In one aspect, the anionic group is located at the para position of each phenyl ring.

The anionic groups are capable of forming covalent bonds with the transition metal (M). Examples of anionic groups that can be present on the corrole include a carboxylate group, a sulfonate group, a boronate group, a sulfate group, a borate group, a phosphonate group, or a phosphate group. The anionic groups of the corrole can be the same or different. In one aspect, the anionic group is a carboxylate group. In another aspect, the anionic group is a carboxylate group at the para position of each phenyl group of TAC.

The selection of the transition metal used to produce the metal-organic framework can vary depending upon the end-use of the metal-organic framework. By varying the transition metal and the anionic groups of the corrole it is possible to produce metal-organic frameworks with varying structural properties and dimensions. Thus, it is possible to fine-tune the metal-organic framework so that it has specific properties.

In one aspect, the metal-organic framework comprises a structural unit comprising the formula I $$M_6(\mu_3\text{—O})_4(\mu_3\text{—OH})_4(OH)_3(H_2O)_3(TCPC)_9 \quad \text{II}$$

wherein M is Zr or Hf, and
TCPC is 5,10,15-tris(p-carboxylphenyl)corrole.

Figure 2A:
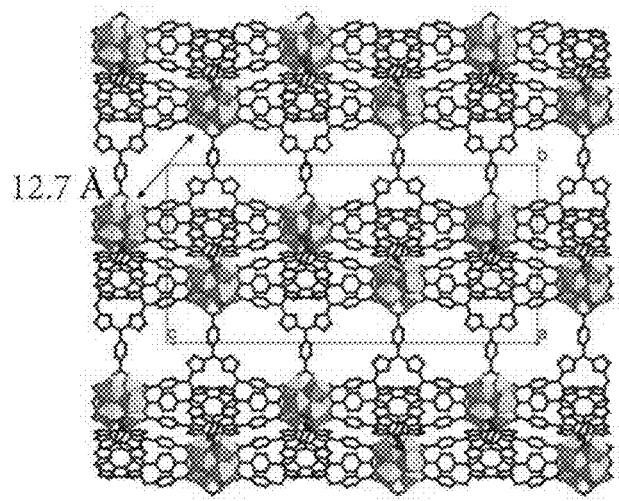
FIGS. 2A-2C shows views of the Corrole-MOF-1 structure along the a (FIG. 2A), b (FIG. 2B) and c (FIG. 2C) axis, respectively.
Figure 2B:
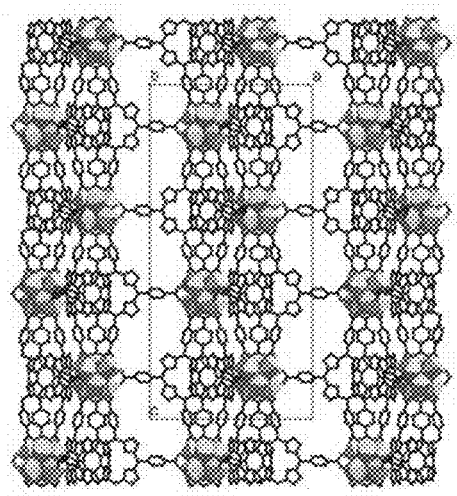
Figure 2C:
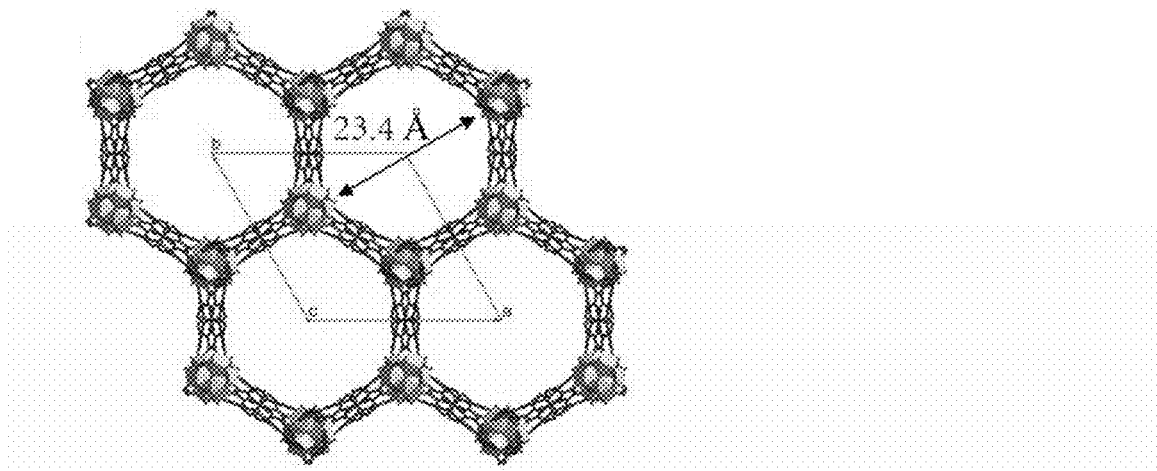

FIGS. 1A-1G and 2A-1C depict an exemplary, non-limiting, metal-organic framework comprising the structural units comprising the formula II, where M is Zr. In this aspect, the metal-organic framework comprises a plurality of structural units of formula II, wherein the structural units are arranged in hexagonal configuration such as the honeycomb configuration provided in FIG. 1D. The structure of the Zr metal-organic framework, which is referred to as Corrole-MOF-1 in FIGS. 1A-1G, involves 9-connected $Zr_6$ $(\mu_3\text{—OH})_4(OH)_3(H_2O)_3(COO)_9$ structural units, which are linked through 3-connected $TCPC^{3-}$ ligands to form a 3D framework containing large hexagonal 1D open channels along the c axis (FIG. 1D, 1E, and FIG. 2C). The structural unit is composed of six Zr atoms assembled into an octahedral $Zr_6(\mu_3\text{—O})_4(\mu_3\text{—OH})_4$ cluster core where only nine edges are bridged by the carboxylates from $TCPC^{3-}$ linkers, while the remaining six positions are occupied by $\mu_3\text{—O}^{2-}$/ $OH^-$ groups (FIG. 1B). The symmetry of the 9-c $Zr_6$ cluster is reduced from $O_h$ to $D_{3d}$, which is affected by the approximately T-shaped geometry of $H_3TCPC$. Topologically, the $H_3TCPC$ ligand and $Zr_6$ cluster can be respectively viewed as 3- and 9-c nodes. In this aspect, the Corrole-MOF-1 framework is classified as a 3D (3,9)-connected gfy net with the point symbol of $(4^{12}.6^{15}.8^9)(4^3)_3$ calculated using the TOPOS program (FIG. 10).

The metal-organic frameworks described herein are three dimensional structures that possess a plurality of pores and channels. FIGS. 2A-2C depict pores and channels in the metal-organic frameworks described herein. Referring to FIGS. 2A and 2B, the metal-organic framework comprises channels along the a and b axis of the framework. In one aspect, the channels have a width along the a and b axis of the framework of from about 10 Å to about 20 Å, or about 10 Å, about 11 Å, about 12 Å, about 13 Å, about 14 Å, about 15 Å, about 16 Å, about 17 Å, about 18 Å, about 19 Å, or about 20 Å, where any value can be a lower and upper endpoint of a range (e.g., about 10 Å to about 19 Å, about 11 Å to about 13 Å, etc.).

In one aspect, the metal-organic frameworks described herein comprise hexagonal channels. An example of this is provided in FIG. 2C. In one aspect, the channels along the c axis have a width of from about 20 Å to about 30 Å, or about 20 Å, about 21 Å, about 22 Å, about 23 Å, about 24 Å, about 25 Å, about 26 Å, about 27 Å, about 28 Å, about 29 Å, or about 30 Å, where any value can be a lower and upper endpoint of a range (e.g., about 21 Å to about 29 Å, about 22 Å to about 26 Å, etc.).

In one aspect, the metal-organic frameworks described herein have a Brunauer-Emmett-Teller (BET) surface area of about 2,500 m$^2$/g to about 2,600 m$^2$/g, or about 2,510 m$^2$/g, about 2,520 m$^2$/g, about 2,530 m$^2$/g, about 2,540 m$^2$/g, about 2,550 m$^2$/g, about 2,560 m$^2$/g, about 2,570 m$^2$/g, about 2,580 m$^2$/g, about 2,590 m$^2$/g, or about 2,600 m$^2$/g, where any value can be a lower and upper endpoint of a range (e.g., about 2,520 m$^2$/g to about 2,590 m$^2$/g, about 2,540 m$^2$/g to about 2,570 m$^2$/g, etc.).

In one aspect, the metal-organic frameworks described herein have a total pore volume of about 1.60 cm$^3$/g to about 1.70 cm$^3$/g, or about 1.60 cm$^3$/g, about 1.61 cm$^3$/g, about 1.62 cm$^3$/g, about 1.63 cm$^3$/g, about 1.64 cm$^3$/g, about 1.65 cm$^3$/g, about 1.66 cm$^3$/g, about 1.67 cm$^3$/g, about 1.68 cm$^3$/g, about 1.69 cm$^3$/g, or about 1.70 cm$^3$/g, where any value can be a lower and upper endpoint of a range (e.g., about 1.61 cm$^3$/g to about 1.69 cm$^3$/g, about 1.63 cm$^3$/g to about 1.66 cm$^3$/g, etc.).

The metal-organic frameworks described herein have high chemical stability in various solvents and aqueous solutions of a wide pH range. The Examples provide evidence of the stability of the metal-organic frameworks. In one aspect, the metal-organic frameworks are stable up to 350° C. under an inert atmosphere.

In other aspects, described herein are methods for producing metal-organic frameworks. In one aspect, the metal-organic framework is produced by reacting $MX_4$ with a corrole having an anionic group on each phenyl ring of the corrole (TAC), wherein M is a transition metal, and X is a leaving group. With respect to $MX_4$, X can be selected based on the nature of transition metal as well as the anionic group on the corrole. In one aspect, X is a halide (e.g., F, Cl, Br, I), an alkoxide (e.g., methoxide, ethoxide), or a nitrate.

In one aspect, $MX_4$ and the corrole having an anionic group on each phenyl ring of the corrole (TAC) are admixed in a solvent and subsequently heated. In one aspect, $MX_4$ and TAC are heated at a temperature of from about 100° C. to about 140° C., or about 100° C., about 105° C., about 110° C., about 115° C., about 120° C., about 125° C., about 130° C., about 135° C., or about 140° C., where any value can be a lower and upper endpoint of a range (e.g., about 100° C. to about 140° C., about 110° C. to about 130° C., etc.). In another aspect, $MX_4$ and TAC are heated at a temperature of from about 100° C. to about 140° C. from about 0.5 minutes to about 100 hours, or about 0.5 minutes, 30 minutes, 1 hour, 10 hours, 25 hours, 50 hours, 75 hours, or 100 hours, where any value can be a lower and upper endpoint of a range (e.g., about 30 minutes to 100 hours, about 50 hours to about 75 hours, etc.).

The relative amount of $MX_4$ and TAC used to produce the metal-organic frameworks can vary. In one aspect, the molar ratio of $MX_4$ to TAC is from about 2:1 to about 4:1, or it is about 2:1, about 2.5:1, about 3:1, about 3.5:1, or about 4:1, where any value can be a lower and upper endpoint of a range (e.g., about 2:1 to about 3.5:1, about 2.5:1 to about 3.5:1, etc.). In another aspect, the molar ratio of $MX_4$ to TAC is about 3:1.

In certain aspects, the metal-organic frameworks described herein can include a transition metal $M^1$ that is coordinated by the corrole (referred to herein as TAC-$M^1$). For example, the transition metal $M^1$ can be coordinated by one or more pyrrole groups of the corrole moiety. The transition metal $M^1$ can be the same or different than the transition metal used to produce the metal-organic framework. Using the conditions provided above (e.g., temperature, duration, solvents, etc.) metal-organic frameworks can be produced with a transition metal $M^1$ coordinated to the corrole. In one aspect, TAC-$M^1$ is [5,10,15-tris(p-carboxylphenyl)corrolato]-$M^1$. In another aspect, TAC-$M^1$ is [5,10,15-tris(p-carboxylphenyl)corrolato]-$M^1$, where $M^1$ is Fe(III) or Fe(IV).

The relative amount of $MX_4$ and TAC-$M^1$ used to produce the metal-organic frameworks can vary. In one aspect, the molar ratio of $MX_4$ to TAC-$M^1$ is from about 2:1 to about 4:1, or it is about 2:1, about 2.5:1, about 3:1, about 3.5:1, or about 4:1, where any value can be a lower and upper endpoint of a range (e.g., about 2:1 to about 3.5:1, about 2.5:1 to about 3.5:1, etc.). In another aspect, the molar ratio of $MX_4$ to TAC-$M^1$ is about 3:1.

In certain aspects, the reaction between $MX_4$ and TAC or TAC-$M^1$ is conducted in a solvent. The selection of the solvent can vary depending upon the solubility of the starting materials. In one aspect, the reaction is conducted in an organic solvent such as, for example, dimethylformamide. The Examples provide non-limiting procedures for isolating and purifying metal-organic framework described herein.

Organic Frameworks

In one aspect, described herein are organic frameworks (referred to herein as COFs). The COFs are crystalline, porous, extended polymers with highly ordered and periodic two-dimensional (2D) or three-dimensional (3D) framework.

Figure 5:
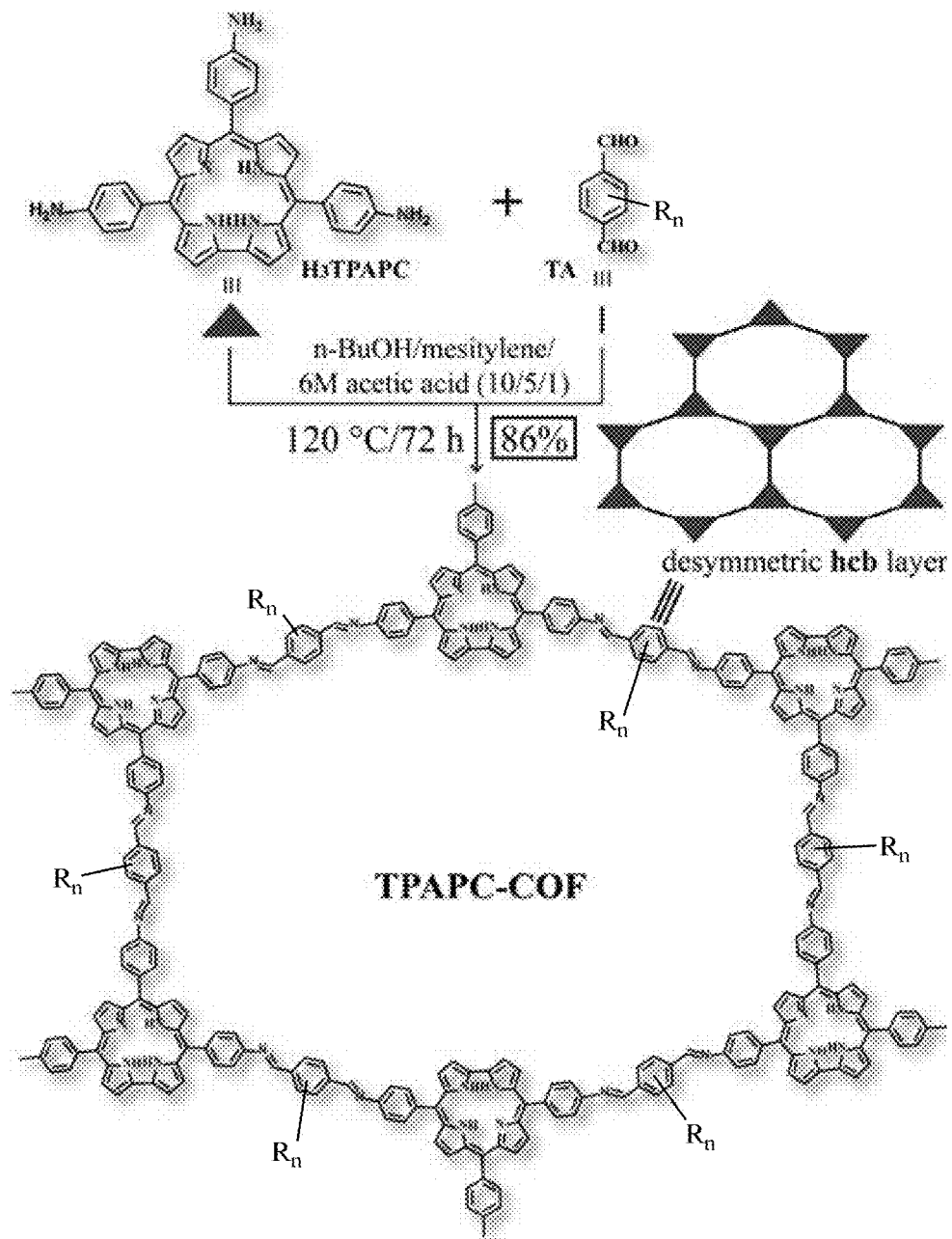
FIG. 5 shows the reaction scheme to produce TPAPC-COF.

In one aspect, the organic framework comprises a structural unit comprising TPAPC-COF as depicted in FIG. 5, where R is hydrogen, an alkyl group, aryl group, an aralkyl group, a halide group, a cyano group, a hydroxy group, alkoxy group, a carboxyl group, a nitro group, or a fused aryl group, and n is an integer from 1 to 4.

Referring to FIG. 5, TPAPC-COF is produced by the condensation reaction between the corrole $H_3$TPAPC and the dialdehyde III. In certain aspects, the dialdehyde III can have one or more fused aryl groups. Examples of fused aryl groups are provided below. It is also possible that one or more of the fused aryl groups contain heteroatoms (i.e., heteroaryl groups). Moreover, the fused aryl groups can be substituted as well (e.g., alkyl group, aryl group).

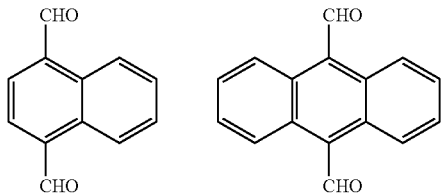 [SMILES: O=Cc1ccc(C=O)c2ccccc12 ; O=Cc1c2ccccc2c(C=O)c2ccccc12]

In one aspect, R is hydrogen and n is 4 in formula III, which is terephthalaldehyde.

FIGS. 6A-6E depict an exemplary, non-limiting, organic framework comprising the structural unit TPAPC-COF. In this aspect, the organic framework comprises a plurality of structural units of TPAPC-COF, wherein the structural units are arranged in hexagonal configuration such as the honeycomb configuration provided in FIGS. 6B and 6D. In one aspect, the organic framework is a two dimensional hcb topology comprising hexagonal one dimensional open channels.

In one aspect, the organic framework comprises an AB stacking structure with elliptical pores, where the AB layers are staggered (FIGS. 6C and 6D).

In one aspect, the organic frameworks described herein are two dimensional structures that possess a plurality of hexagonal channels. In one aspect, the hexagonal channels have a pore size of about 10 Å to about 20 Å, or about 10 Å, about 11 Å, about 12 Å, about 13 Å, about 14 Å, about 15 Å, about 16 Å, about 17 Å, about 18 Å, about 19 Å, or about 20 Å, where any value can be a lower and upper endpoint of a range (e.g., about 10 Å to about 19 Å, about 11 Å to about 13 Å, etc.).

In one aspect, the organic frameworks described herein have a Brunauer-Emmett-Teller (BET) surface area of about 700 $m^2/g$ to about 800 $m^2/g$, or about 700 $m^2/g$, about 710 $m^2/g$, about 720 $m^2/g$, about 730 $m^2/g$, about 740 $m^2/g$, about 750 $m^2/g$, about 760 $m^2/g$, about 770 $m^2/g$, about 780 $m^2/g$, about 790 $m^2/g$, or about 800 $m^2/g$, where any value can be a lower and upper endpoint of a range (e.g., about 710 $m^2/g$ to about 790 $m^2/g$, about 720 $m^2/g$ to about 760 $m^2/g$, etc.).

In one aspect, the organic frameworks described herein have a total pore volume of about 0.40 $cm^3/g$ to about 0.50 $cm^3/g$, or about 0.40 $cm^3/g$, about 0.41 $cm^3/g$, about 0.42 $cm^3/g$, about 0.43 $cm^3/g$, about 0.44 $cm^3/g$, about 0.45 $cm^3/g$, about 0.46 $cm^3/g$, about 0.47 $cm^3/g$, about 0.48 $cm^3/g$, about 0.49 $cm^3/g$, or about 0.50 $cm^3/g$, where any value can be a lower and upper endpoint of a range (e.g., about 0.41 $cm^3/g$ to about 0.49 $cm^3/g$, about 0.43 $cm^3/g$ to about 0.46 $cm^3/g$, etc.).

In one aspect, the organic frameworks are stable up to 400° C. under an inert atmosphere.

In other aspects, described herein are methods for producing organic frameworks, which comprises reacting 5,10, 15-tris(p-aminophenyl)corrole ($H_3$TPAPC) with the dialdehyde of formula III.

In one aspect, $H_3$TPAPC and the dialdehyde of formula III are admixed in a solvent and subsequently heated. In one aspect, $H_3$TPAPC and the dialdehyde are heated at a temperature of from about 100° C. to about 140° C., or about 100° C., about 105° C., about 110° C., about 115° C., about 120° C., about 125° C., about 130° C., about 135° C., or about 140° C., where any value can be a lower and upper endpoint of a range (e.g., about 100° C. to about 140° C., about 110° C. to about 130° C., etc.). In another aspect, $H_3$TPAPC and the dialdehyde are heated at a temperature of from about 100° C. to about 140° C. from about 0.5 minutes to about 100 hours, or about 0.5 minutes, 30 minutes, 1 hour, 10 hours, 25 hours, 50 hours, 75 hours, or 100 hours, where any value can be a lower and upper endpoint of a range (e.g., about 30 minutes to 100 hours, about 50 hours to about 75 hours, etc.).

The relative amount of the dialdehyde of formula III and $H_3$TPAPC used to produce the metal-organic frameworks can vary. In one aspect, the molar ratio of the dialdehyde of formula III and $H_3$TPAPC is from about 1:1 to about 2:1, or it is about 1:1, about 1.25:1, about 1.5:1, about 1.75:1, or about 2:1, where any value can be a lower and upper endpoint of a range (e.g., about 1:1 to about 1.75:1, about 1.25:1 to about 1.5:1, etc.). In another aspect, the molar ratio of the dialdehyde of formula III and $H_3$TPAPC is about 1.5:1.

In one aspect, the reaction between 5,10,15-tris(p-aminophenyl)corrole ($H_3$TPAPC) with the dialdehyde of formula III is conducted in the presence of a solvent. The selection of the solvent can vary depending upon the solubility of the starting materials. In one aspect, the reaction is conducted in a solvent comprising a mixture of n-butyl alcohol, mesitylene, and acetic acid. The Examples provide non-limiting procedures for isolating and purifying the organic frameworks described herein.

Applications of Frameworks

Due to their unique structures and physical properties, the frameworks described herein can be used in numerous applications. In one aspect, the frameworks described herein can be used in the fields of gas storage/separation, proton conduction, biological and medical applications, chemical sensors, energy conversion, optoelectronics, and catalysis.

In one aspect, the frameworks described herein are useful heterogeneous catalysts in Diels-Alder reactions. In another aspect, the metal-organic frameworks described are useful catalysts in hetero-Diels-Alder reactions. Not wishing to be bound by theory, the high porosity of the metal-organic frameworks can facilitate mass transport and maximize the accessibility of catalytic sites.

In one aspect, the method involves reacting a diene and dienophile in the presence of a catalytic amount (0.5 to 5 mol %) of the metal-organic framework. The Examples provide non-limiting procedures for conducting the Diels-Alder reaction. The ability of the metal-organic frameworks to facilitate hetero-Diels-Alder reactions makes them quite useful in organic synthesis. A wide variety of heterocycles can be produced using the metal-organic framework as a catalyst. For example, when the dienophile is a compound such as an aldehyde, a ketone, an imine, a thioaldehyde, a thioketone, or an alkene (e.g., linear or cyclic), a wide variety of different compounds can be produced. For example, as shown in the Examples, when unsubstituted or substituted benzaldehyde is used as the dienophile, a variety of different dihydropyrans can be synthesized in high yield. A variety of different dienes can be used as well, including unsubstituted or substituted (e.g., alkyl, aryl, etc.) butadiene. Furthermore, owing to the high stability of the metal-organic frameworks, the frameworks can be recycled and maintain high catalytic activity with retention of structural integrity.

In other aspects, the frameworks described herein possess optoelectronic properties. Not wishing to be bound by theory, the organic frameworks described herein have favorable electron delocalization on the polymeric backbone with extended 7-conjugations and layer stacking architectures, forming periodic columnar 7-arrays with significant electronic overlap.

In one aspect, the organic frameworks described herein can generate singlet oxygen when irradiated. The development of methodologies for efficiently producing $^1O_2$ has numerous applications in photodynamic therapy. In one aspect, the organic framework can produce singlet oxygen when irradiated by a laser or a xenon lamp at a wavelength of about 200 nm to about 2,000 nm, or about 200 nm, about 300 nm, about 400 nm, about 500 nm about, about 600 nm, about 700 nm, about 800 nm, about 900 nm, about 1,000 nm, about 1,200 nm, about 1,400 nm, about 1,600 nm, or about 2,000 nm, where any value can be a lower and upper endpoint of a range (e.g., about 300 nm to 1,800 nm, about 500 nm to about 800 nm, etc.).

Due to the ability of the organic frameworks described herein to generate singlet oxygen, the organic frameworks are useful in photodynamic therapy. In one aspect, the organic frameworks can be used to damage cancer cells, wherein the method involves irradiating the cancer cells in the presence of the organic framework. In one aspect, the cancer cells are killed. In other aspects, the activity of the cancer cells is decreased (e.g., ability to grow or develop further cells). In addition to damaging cancer cells, the organic frameworks have minimal to no cytotoxicity, which is demonstrated in the Examples.

In another aspect, the organic frameworks described herein are useful in treating cancer in a subject, wherein the method comprises (1) administering the organic framework to the subject and (2) irradiating the organic framework.

The organic frameworks described herein can be combined with at least one pharmaceutically-acceptable carrier to produce a pharmaceutical composition. The pharmaceutical compositions can be prepared using techniques known in the art. In one aspect, the pharmaceutical composition is prepared by admixing the organic frameworks with a pharmaceutically-acceptable carrier.

Pharmaceutically-acceptable carriers are known to those skilled in the art. These most typically would be standard carriers for administration to humans and/or other mammals, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents, and the like, in addition to the organic frameworks described herein. Pharmaceutical compositions may also include one or more additional active ingredients such as antimicrobial agents, anti-inflammatory agents, anesthetics, and the like.

The pharmaceutical composition may be administered in a number of ways depending on whether local or systemic treatment is desired, and on the area to be treated. Administration may be parenterally, orally, subcutaneously, intralesionally, intraperitoneally, intravenously, or intramuscularly.

Preparations for administration include sterile aqueous or non-aqueous solutions, suspensions, and emulsions. Examples of non-aqueous carrier include alcoholic/aqueous solutions, emulsions, or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, antioxidants, chelating agents, inert gases, and the like.

In certain aspects, it may be desirable to increase the hydrophilicity of the pharmaceutical composition that includes the organic framework. In one aspect, the pharmaceutical composition includes a hydrophilic compound. For example, the hydrophilic compound can be a polyalkylene glycol. "Polyalkylene glycol" as used herein refers to a condensation polymer of ethylene oxide or propylene oxide and water. Polyalkylene glycols are typically colorless liquids with high molecular weights and are soluble in water as well as some organic solvents. In one aspect, the polyalkylene glycol is polyethylene glycol and/or polypropylene glycol. In another aspect, the polyalkylene glycol is monomethoxy polyethylene glycol.

In a further aspect, polyalkylene glycols are of low enough molecular weight that the chemical nature of the end groups (usually, but not always, hydroxyls) still affects the performance of the framework. In addition to being hydrophilic, polyalkylene glycols can modify the viscosity of the frameworks disclosed herein and may aid in the formation of emulsions. In another aspect, polyalkylene glycols are biocompatible and/or biodegradable. In still another aspect, the polyalkylene glycols and/or other hydrophilic groups used herein are non-toxic.

Pharmaceutical compositions comprising the frameworks described herein can be administered to a subject using techniques known in the art. In one aspect, the framework can be injected into a solid tumor followed by irradiating the tumor as discussed above. In one aspect, the cancer can be pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumors.

Aspects

The following listing of exemplary aspects supports and is supported by the disclosure provided herein.

Aspect 1. A metal-organic framework comprising a structural unit comprising the formula I $$M_6(\mu_3-O)_4(\mu_3-OH)_4(OH)_3(H_2O)_3(TAC)_9 \qquad I$$

wherein M is a transition metal, and
TAC is a 5,10,15-tris(phenyl)corrole with an anionic group on each phenyl ring of the corrole.

Aspect 2. The metal-organic framework according to Aspect 1, wherein the anionic group is located at the para position of each phenyl ring.

Aspect 3. The metal-organic framework according to Aspects 1 or 2, wherein the anionic group comprises a carboxylate group, a sulfonate group, a boronate group, a sulfate group, a borate group, a phosphonate group, or a phosphate group.

Aspect 4. The metal-organic framework according to Aspects 1-3, wherein the anionic group is the same group.

Aspect 5. The metal-organic framework according to Aspects 1-4, wherein the anionic group is a carboxylate group.

Aspect 6. The metal-organic framework according to Aspects 1-5, wherein M is Zr or Hf.

Aspect 7. The metal-organic framework according to Aspects 1-6, wherein the metal-organic framework comprises a structural unit comprising the formula II $$M_6(\mu_3-O)_4(\mu_3-OH)_4(OH)_3(H_2O)_3(TCPC)_9 \quad \text{II}$$

wherein M is Zr or Hf, and
TCPC is 5,10,15-tris(p-carboxylphenyl)corrole.

Aspect 8. The metal-organic framework according to Aspects 1-7, wherein the framework comprises a plurality of structural units of formula I or II, wherein the structural units are arranged in hexagonal configuration.

Aspect 9. The metal-organic framework according to Aspects 1-7, wherein the framework comprises a plurality of structural units of formula I or II, wherein the structural units are arranged in honeycomb configuration.

Aspect 10. The metal-organic framework according to Aspects 1-7, wherein the framework is a three dimensional (3,9)-connected gfy topology comprising hexagonal one dimensional open channels.

Aspect 11. The metal-organic framework according to Aspects 1-10, wherein the framework has a Brunauer-Emmett-Teller (BET) surface area of about 2,500 $m^2/g$ to about 2,600 $m^2/g$.

Aspect 12. The metal-organic framework according to Aspects 1-11, wherein the framework has a total pore volume of about 1.60 $cm^3/g$ to about 1.70 $cm^3/g$.

Aspect 13. The metal-organic framework according to Aspects 1-12, wherein the framework comprises hexagonal channels, wherein the pore size of the hexagonal channels is from about 20 Å to about 30 Å.

Aspect 14. The metal-organic framework according to Aspects 1-13, wherein the framework comprises channels along the a and b axis of the framework, wherein the channels have a width of from about 10 Å to about 20 Å.

Aspect 15. The metal-organic framework according to Aspects 1-14, wherein the framework is stable up to 350° C. under an inert atmosphere.

Aspect 16. The metal-organic framework according to Aspects 1-15, wherein the framework further comprises a transition metal $M^1$, wherein the transition metal is coordinated by one or more pyrrole groups of the corrole moiety.

Aspect 17. The metal-organic framework according to Aspect 16, wherein transition metal $M^1$ is different than M.

Aspect 18. The metal-organic framework according to Aspect 16, wherein transition metal $M^1$ is the same as M.

Aspect 19. The metal-organic framework according to Aspects 16-18, wherein the transition metal is Fe(III) or Fe(IV).

Aspect 20. A metal-organic framework produced by reacting $MX_4$ with a corrole having an anionic group on each phenyl ring of the corrole (TAC), wherein M is a transition metal, and X is a leaving group.

Aspect 21. The metal-organic framework according to Aspect 20, wherein the anionic group is located at the para position of each phenyl ring.

Aspect 22. The metal-organic framework according to Aspects 20 or 21, wherein the anionic group comprises a carboxylate group, a sulfonate group, a boronate group, a sulfate group, a borate group, a phosphonate group, or a phosphate group.

Aspect 23. The metal-organic framework according to Aspects 20-22, wherein the anionic group is the same group.

Aspect 24. The metal-organic framework according to Aspects 20-23, wherein the anionic group is a carboxylate group.

Aspect 25. The metal-organic framework according to Aspects 20-24, wherein M is Zr or Hf.

Aspect 26. The metal-organic framework according to Aspects 20-25, wherein X is a halide, alkoxide, or a nitrate.

Aspect 27. The metal-organic framework according to Aspects 20-26, wherein TAC is 5,10,15-tris(p-carboxylphenyl)corrole ($H_3$TCPC) and M is Zr or Hf.

Aspect 28. The metal-organic framework according to Aspect 27, wherein $MX_4$ and TAC are admixed in a solvent and heated at a temperature of from about 100° C. to about 140° C. from about 0.5 minutes to about 100 hours.

Aspect 29. The metal-organic framework according to Aspects 27 or 28, wherein the molar ratio of $MX_4$ to TAC is from about 2:1 to about 4:1.

Aspect 30. The metal-organic framework according to Aspects 27 or 28, wherein the molar ratio of $MX_4$ to TAC is about 3:1.

Aspect 31. A metal-organic framework produced by reacting $MX_4$ with a corrole having an anionic group on each phenyl ring of the corrole and a transition metal $M^1$ coordinated to the corrole (TAC-$M^1$).

Aspect 32. The metal-organic framework according to Aspect 31, wherein TAC-$M^1$ is [5,10,15-tris(p-carboxylphenyl)corrolato]-$M^1$, wherein M is Zr or Hf.

Aspect 33. The metal-organic framework according to Aspect 31, wherein $MX_4$ and TAC-$M^1$ are admixed in a solvent and heated at a temperature of from 100° C. to 140° C. from 0.5 minutes to 100 hours.

Aspect 34. The metal-organic framework according to Aspects 31 or 32, wherein the molar ratio of $MX_4$ to TAC-$M^1$ is from 2:1 to 4:1.

Aspect 35. The metal-organic framework according to Aspects 31 or 32, wherein the molar ratio of $MX_4$ to TAC-$M^1$ is about 3:1.

Aspect 36. The metal-organic framework according to Aspects 31 or 32, wherein the molar ratio of $MX_4$ to [5,10,15-tris(p-carboxylphenyl)corrolato]-$M^1$ is from 2:1 to 4:1.

Aspect 37. The metal-organic framework according to Aspects 31 or 32, wherein the molar ratio of $MX_4$ to [5,10,15-tris(p-carboxylphenyl)corrolato]-$M^1$ is about 3:1.

Aspect 38. The metal-organic framework according to Aspects 31-37, wherein $M^1$ is Fe(III) or Fe(IV).

Aspect 39. The use of the metal-organic framework according to Aspects 1-38 or 49-67 in gas storage/separation, proton conduction, biomedicine, sensing, and catalysis.

Aspect 40. The use of the metal-organic framework according to Aspects 1-38 or 49-67 as a catalyst in a Diels-Alder reaction.

Aspect 41. The use according to Aspect 40, wherein the Diels-Alder reaction is a hetero-Diels-Alder reaction.

Aspect 42. A method for conducting a Diels-Alder reaction, comprising reacting a diene and dienophile in the presence of the metal-organic framework according to Aspects 1-38 or 49-67.

Aspect 43. The method according to Aspect 42, wherein the dienophile is an aldehyde, a ketone, an imine, a thioaldehyde, a thioketone, or an alkene.

Aspect 44. The method according to Aspects 42 or 43, wherein the dienophile is an unsubstituted or substituted benzaldehyde.

Aspect 45. The method according to Aspects 42-44, wherein the diene is unsubstituted or substituted butadiene.

Aspect 46. The method according to Aspects 42-45, wherein the metal-organic framework comprises a structural unit comprising the formula I $$M_6(\mu_3-O)_4(\mu_3-OH)_4(OH)_3(H_2O)_3(TCPC)_9 \quad \text{I}$$

wherein M is Zr or Hf, and
sTCPC is 5,10,15-tris(p-carboxylphenyl)corrole.

Aspect 47. The method according to Aspects 42-46, wherein the framework further comprises a transition metal, wherein the transition metal is coordinated by one or more pyrrole groups of the corrole moiety.

Aspect 48. The method according to Aspect 47, wherein the transition metal is Fe(III) or Fe(IV).

Aspect 49. An organic framework comprising a structural unit comprising TPAPC-COF as depicted in FIG. 5, wherein R is hydrogen, an alkyl group, aryl group, an aralkyl group, a halide group, a cyano group, a hydroxy group, alkoxy group, a carboxyl group, or a nitro group, or a fused aryl group, and n is an integer from 1 to 4.

Aspect 50. The organic framework according to Aspect 49, wherein R is hydrogen and n is 4.

Aspect 51. The organic framework according to Aspects 49 or 50, wherein the framework comprises a plurality of structural units of TPAPC-COF, wherein the structural units are arranged in hexagonal configuration.

Aspect 52. The organic framework according to Aspects 49 or 50, wherein the framework comprises a plurality of structural units of TPAPC-COF, wherein the structural units are arranged in honeycomb configuration.

Aspect 53. The organic framework according to Aspects 49 or 50, wherein the framework is a two dimensional hcb topology comprising hexagonal one dimensional open channels.

Aspect 54. The organic framework according to Aspects 49 or 50, wherein the framework comprises an AB stacking structure with elliptical pores.

Aspect 55. The organic framework according to Aspects 49-54, wherein the framework has a Brunauer-Emmett-Teller (BET) surface area of about 700 $m^2/g$ to about 800 $m^2/g$.

Aspect 56. The organic framework according to Aspects 49-54, wherein the framework has a total pore volume of about 0.4 $cm^3/g$ to about 0.5 $cm^3/g$.

Aspect 57. The organic framework according to Aspects 49-54, wherein the framework comprises hexagonal channels, wherein the pore size of the hexagonal channels is from about 10 Å to about 20 Å.

Aspect 58. The organic framework according to Aspects 49-54, wherein the framework is stable up to 400° C. under an inert atmosphere.

Aspect 59. An organic framework produced by reacting 5,10,15-tris(p-aminophenyl)corrole ($H_3$TPAPC) with a compound of formula III

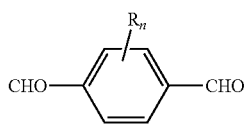

III wherein R is hydrogen, an alkyl group, aryl group, an aralkyl group, a halide group, a cyano group, a hydroxy group, alkoxy group, a carboxyl group, or a nitro group, or a fused aryl group, and n is an integer from 1 to 4.

Aspect 60. The organic framework according to Aspect 59, wherein R is hydrogen and n is 4.

Aspect 61. The organic framework according to Aspects 59 or 60, wherein the compound of formula II and 5,10,15-tris(p-aminophenyl)corrole are admixed in a solvent and heated at a temperature of from about 100° C. to about 140° C. from about 0.5 minutes to about 100 hours.

Aspect 62. The organic framework according to Aspects 59-61, wherein the molar ratio of the compound of formula III to 5,10,15-tris(p-aminophenyl)corrole is from about 1:1 to about 2:1.

Aspect 63. The organic framework according to Aspects 59-61, wherein the molar ratio of the compound of formula III to 5,10,15-tris(p-aminophenyl)corrole is about 1.5:1.

Aspect 64. The organic framework according to Aspects 59-63, wherein the reaction is conducted in a solvent comprising a mixture of n-butyl alcohol, mesitylene, and acetic acid.

Aspect 65. The organic framework according to Aspects 59-64, wherein the framework further comprises a hydrophilic compound.

Aspect 66. The organic framework according to Aspect 65, wherein the hydrophilic compound comprises a polyalkylene glycol.

Aspect 67. The organic framework according to Aspect 66, wherein the polyalkylene glycol is a polyethylene glycol, polypropylene glycol, or a monomethoxy polyethylene glycol.

Aspect 68. The use of the organic framework according to Aspects 1-67 in a chemical sensor, energy conversion, optoelectronics, biological and medical applications, gas storage/separation, and catalysis.

Aspect 69. A method for generating singlet oxygen, the method comprising irradiating the organic framework according to Aspects 1-67.

Aspect 70. The method according to Aspect 69, wherein the organic framework is irradiated by a laser or a xenon lamp.

Aspect 71. The method according to Aspects 68 or 69, wherein the organic framework is irradiated at a wavelength of about 200 nm to about 2,000 nm.

Aspect 72. A method for damaging cancer cells, the method comprising irradiating the cancer cells in the presence of the organic framework according to Aspects 1-67.

Aspect 73. The method according to Aspect 72, wherein the cancer cells are killed.

Aspect 74. The method according to Aspect 72, wherein the activity of the cancer cells is decreased.

Aspect 75. The method according to Aspect 72-74, wherein the organic framework is irradiated by a laser or a xenon lamp.

Aspect 76. The method according to Aspects 72-75, wherein the organic framework is irradiated at a wavelength of about 200 nm to about 2,000 nm.

Aspect 77. A method for treating cancer in a subject, the method comprising (1) administering the organic framework according to Aspects 1-67 to the subject and (2) irradiating the organic framework.

Aspect 78. The method according to Aspect 77, wherein the organic framework is irradiated by a laser.

Aspect 79. The method according to Aspects 77 or 78, wherein the organic framework is irradiated at a wavelength of about 200 nm to about 2,000 nm.

Aspect 80. A method for generating singlet oxygen, the method comprising irradiating the organic framework in any one of Aspects 1-67.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the product purity and yield obtained from the described process. Only reasonable and routine experimentation will be required to optimize such process conditions.

Preparation and Evaluation of Metal-Organic Frameworks

General Information. The commercial chemicals are used as purchased unless otherwise mentioned. The $H_3TCPC$ and FeTCPCCl ligands were prepared according to procedures described in Section 1, Supporting Information (SI).

Instrumentation. Powder X-ray diffraction (PXRD) data were collected on a Bruker AXS D8 Advance A25 Powder X-ray diffractometer (40 kV, 40 mA) using Cu Kα ($\lambda$=1.5406 Å) radiation. Gas sorption isotherm measurements were carried out on the Micromeritics ASAP 2020 with different temperatures. $N_2$ isotherms were performed at 77 K, with the temperature held constant using liquid $N_2$ bath. Fourier transform infrared spectra (FTIR) were recorded on a Nicolet Impact 410 FTIR spectrometer. Thermogravimetric analyses (TGA) were carried out on a Q50 thermogravimetric analyzer in nitrogen atmosphere. Elemental analyses were performed on a Perkin-Elmer series II CHNS analyzer 2400. Nuclear magnetic resonance (NMR) data were recorded on a Bruker Avance-400 (400 MHz) spectrometer. MALDI-TOF-MS was obtained with a Bruker Autoflex TOF/TOF III instrument. UV-Vis absorption spectra were conducted on a JASCO model V-670 spectrometer. Scanning electron microscopy (SEM) images and energy dispersive spectrometer (EDS) analyses were performed on a Hitachi SU 8000. All the Corrole-MOFs were activated by supercritical $CO_2$ performing on a Tousimis™ Samdri® PVT-30 critical point dryer.

Synthesis of 5,10,15-Tris(p-carboxymethylphenyl)corrole ($H_3TCMPC$) Methyl p-formylbenzoate (5 mmol, 821 mg) and pyrrole (10 mmol, 697 μL) were dissolved in 200 ml MeOH, and then 200 ml $H_2O$ was added. Subsequently, 4.25 ml concentrated HCl was added, and the reaction was stirred at room temperature for 3 h. After that, the mixture was extracted with $CHCl_3$, and the organic layer was washed twice with $H_2O$, dried ($MgSO_4$), filtered, and diluted to 300 mL with $CHCl_3$. Chloranil (5 mmol, 1.23 g) was added, and the mixture was refluxed for 2 h. The reaction mixture was evaporated to dryness, and the crude product was purified by chromatography (silica gel) with $CHCl_3$, DCM/EA (30:1, by vol.) and DCM successively, finally with pure green product obtained (240 mg, 20.6% yield). UV-Vis ($CH_2Cl_2$) $\lambda_{max}$: 426, 583, 622, 653 nm; $^1H$ NMR (400 MHz, $CDCl_3$) δ: 8.75 (s, 4H), 8.63; (s, 6H), 8.42; (d, J 12, 4H), 8.29; (s, 4H), 8.19; (s, 2H), 3.37; (s, 9H), -2.26; (s, 3H); MALDI-TOF-MS: m/z calcd for $C_{43}H_{32}N_4O_6$, 700.23; found, 700.47 [M+H]$^+$.

Synthesis of [5,10,15-Tris(p-carboxymethylphenyl)corrolato]-Fe(IV) Chloride (FeTCMPCCl). A solution of $H_3TCMPC$ (70 mg, 0.10 mmol), $FeCl_2.4H_2O$ (398 mg, 2.0 mmol), and DMF (8 mL) was refluxed under nitrogen for 2 h in the dark. After cooling to room temperature, 15 ml HCl aqueous solution (3 mol/L) was dropwise added to the mixture. The resulted precipitate was filtrated and dissolved in $CH_2Cl_2$ (20 mL) and washed with 7% aqueous HCl (15 mL×3). The organic layer was dried over $MgSO_4$, filtered, and concentrated under reduced pressure to give the target compound as a dark brown solid (63 mg, 80% yield). UV-Vis ($CH_2Cl_2$) $\lambda_{max}$: 363, 408, 632 nm; MALDI-TOF-MS: m/z calcd for $C_{43}H_{29}ClFeN_4O_6$, 788.11; found, 788.30 [M+H]$^+$.

Synthesis of 5,10,15-Tris(p-carboxylphenyl)corrole ($H_3TCPC$). The obtained $H_3TCMPC$ (300 mg, 0.43 mmol) was stirred in 350 mL THF and 350 mL MeOH mixed solvent, to which a solution of KOH (7.15 g, 127.68 mmol) in 100 mL $H_2O$ was introduced. The mixture was heated at 40° C. for 24 h. After cooling down to room temperature, the resulting mixture was acidified with 6 mol/L HCl with pH≤3. Then the mixed solution was extracted with $CH_2Cl_2$. After evaporated to dryness, the resulted crude product was chromatographed with THF/MeOH (20:1, by vol.) to give pure product $H_3TCPC$ (257 mg, 91% yield). MALDI-TOF-MS: m/z calcd for $C_{40}H_{26}N_4O_6$, 658.19; found, 658.51 [M+H]$^+$.

Synthesis of [5,10,15-Tris(p-carboxylphenyl)corrolato]-Fe(IV) Chloride (FeTCPCCl). The obtained FeTCMPCCl (321 mg, 0.43 mmol) was stirred in 350 mL THF and 350 mL MeOH mixed solvent, to which a solution of KOH (7.15 g, 127.68 mmol) in 100 mL $H_2O$ was introduced. The mixture was heated at 40° C. for 24 h. After cooling down to room temperature, the resulting mixture was acidified with 6 mol/L HCl with pH≤3. Then the mixed solution was extracted with $CH_2Cl_2$. After evaporated to dryness, the resulted crude product was chromatographed with THF/MeOH (20:1, by vol.) to give pure product FeTCPCCl (279 mg, 87% yield). MALDI-TOF-MS: m/z calcd for $C_{40}H_{23}ClFeN_4O_6$, 746.07; found, 746.28 [M+H]$^+$.

Synthesis of Corrole-MOF-1. In a 5 mL glass vial, $ZrCl_4$ (0.054 mmol, 3.0 equiv), $H_3TCPC$ (0.018 mmol, 1.0 equiv) and benzoic acid (1.8 mmol, 100 equiv) were dissolved in N,N-dimethylformamide (DMF, 1.0 mL) via sonication (30 min). The green solution was heated at 120° C. for 72 h in an oven. After cooling down to room temperature, hexagonal purple crystals were harvested by filtration (Yield. 87%). Anal. Calcd (%): C, 52.77; H, 2.20; N, 6.16. Found: C, 52.03; H, 2.36; N, 6.01.

Synthesis of Corrole-MOF-2. In a 5 mL glass vial, $HfCl_4$ (0.054 mmol, 3.0 equiv), $H_3TCPC$ (0.018 mmol, 1.0 equiv) and benzoic acid (1.8 mmol, 100 equiv) were dissolved in DMF (1.0 mL) via sonication (30 min). The green solution was heated at 120° C. for 72 h in an oven. After cooling down to room temperature, hexagonal purple crystals were harvested by filtration (Yield. 73%). Anal. Calcd (%): C, 44.28; H, 1.85; N, 5.17. Found: C, 44.73; H, 1.92; N, 4.98.

Synthesis of Corrole-MOF-1(Fe). In a 5 mL glass vial, $ZrCl_4$ (0.054 mmol, 3.0 equiv), FeTCPCCl (0.018 mmol, 1.0 equiv) and acetic acid (7.87 mmol, 437 equiv) were dissolved in DMF (1.0 mL) via sonication (30 min). The brown solution was heated at 120° C. for 72 h in an oven. After cooling down to room temperature, brown powders were obtained for characterization (Yield. 84%). Anal. Calcd (%): C, 51.10; H, 2.02; N, 5.96. Found: C, 51.46; H, 2.13; N, 5.77. Purple hexagonal single crystals of Corrole-MOF-1 and -2 with suitable sizes for single-crystal X-ray diffraction have been obtained in our experiments. Corrole-MOF-1(Fe) was confirmed by powder X-ray diffraction pattern.

Single-Crystal X-ray Crystallography. The X-ray diffraction data for Corrole-MOF-1 were measured on Bruker D8 Venture PHOTON II CPAD system equipped with a Cu Kα INCOATEC ImuS micro-focus source ($\lambda$=1.54178 Å). The X-ray diffraction data for Corrole-MOF-2 were collected using synchrotron radiation (λ=0.41328 Å) at Advanced Photon Source, Beamline 15-ID-B of ChemMatCARS in Argonne National Lab, Argonne, Ill. Indexing was performed using APEX3 (Difference Vectors method). Data integration and reduction were performed using SaintPlus. Absorption correction was performed by multi-scan method implemented in SADABS. Space groups were determined using XPREP implemented in APEX3. Structures were solved using SHELXT and refined using SHELXL-2018 (full-matrix least-squares on $F^2$) through OLEX2 interface program.

Corrole-MOF-1 and -2 crystals (constructed from $Zr_6$ and $Hf_6$ clusters, respectively) are isostructural. In both cases diffraction frames contain diffuse streaks/lines and reflections are visibly clustered into groups. Both structures were modeled in highest symmetry ($P6_3/mmc$) suggested by data analyses, which is consistent with observed ligand and cluster disorder over two positions. The observed disorder could possibly be due to two possible conformations of benzoate part perpendicular to c crystallographic direction that would result in two possible orientations of metal cluster rotated by 60°. Disordered atoms were refined with restraints. The contribution of disordered content in structural voids in both cases was treated as diffuse using Squeeze procedure implemented in Platon program. Crystallographic data and structural refinements for Corrole-MOF-1 and -2 are summarized in Table S1, SI. The CIF file can be obtained free of charge from the Cambridge Crystallographic Data Centre via www.ccdc.cam.ac.uk/data_request/cif (CCDC 1939968 for Corrole-MOF-1, 1939478 for Corrole-MOF-2). The crystal data for Corrole-MOF-1 and Corrole-MOF-2 are provided in Table 1.

TABLE 1

Crystal Data for Corrole-MOF-1 and -2

| | Corrole-MOF-1 | Corrole-MOF-2 |
|---|---|---|
| Formula | $C_{120}H_{60}N_{12}O_{32}Zr_6$ | $C_{120}H_{60}N_{12}O_{32}Hf_6$ |
| $F_w$ | 2729.12 | 3252.74 |
| T (K) | 100.02 | 100.02 |
| Crystal system | hexagonal | hexagonal |
| Space group | $P6_3/mmc$ | $P6_3/mmc$ |
| a, c (Å) | 28.6282(14), 25.6439(12) | 28.6282(14), 25.6439(12) |
| α, γ (deg) | 90, 120 | 90, 120 |
| V (Å$^3$) | 18201 (2) | 18201(2) |
| Z | 2 | 2 |
| $d_{calc}$ (g/cm$^3$) | 0.498 | 0.594 |
| μ (mm$^{-1}$) | 1.587 | 0.385 |
| F(000) | 2720.0 | 3104.0 |
| Radiation | CuKα (λ = 1.54178) | Synchrotron (λ = 0.41328) |
| 2θ range for data collection/° | 4.958 to 149.216 | 1.654 to 24.566 |
| Collected reflections | 259551 | 218346 |
| Independent reflections | 6739 | 3781 |
| $R_{int}$, $R_{sigma}$ | 0.1269, 0.0256 | 0.1905, 0.0632 |
| Data/restraints/parameters | 6739/81/274 | 3781/616/272 |
| GOF on $F^2$ | 1.192 | 1.040 |
| $R_1$, $wR_2$ [$I > 2σ (I)$] | 0.0871, 0.2788 | 0.0879, 0.2468 |
| $R_1$, $wR_2$ (all data) | 0.1144, 0.3285 | 0.1384, 0.3126 |
| $Δρ_{max}/Δρ_{min}$ (e · Å$^{-3}$) | 0.71/−0.85 | 0.94/−0.52 |

Single-crystal X-ray diffraction studies revealed that both Corrole-MOF-1 and -2 crystallize in the hexagonal space group $P6_3/mmc$. The structure of Corrole-MOF-1 involves 9-connected $Zr_6(μ_3-O)_4(μ_3-OH)_4(OH)_3(H_2O)_3(COO)_9$ SBUs, which are linked through 3-connected $TCPC^{3-}$ ligands to form a 3D framework containing large hexagonal 1D open channels along the c axis (FIGS. 1D and 1E). The SBU is composed of six Zr atoms assembled into an octahedral $Zr_6(μ_3-O)_4(μ_3-OH)_4$ cluster core where only nine edges are bridged by the carboxylates from $TCPC^{3-}$ linkers, while the remaining six positions are occupied by $μ_3-O^{2-}/OH^-$ groups (FIG. 1B). Compared with the well-known 12-c $Zr_6$ cluster,[32] the symmetry of the 9-c $Zr_6$ cluster is reduced from $O_h$ to $D_{3d}$, which is affected by the approximately T-shaped geometry of $H_3TCPC$. The solvent-accessible volume in Corrole-MOF-1 and -2 is calculated to be 68.8 and 68.5% respectively, using the PLATON routine.[33] Topologically, the $H_3TCPC$ ligand and $Zr_6$ cluster can be respectively viewed as 3- and 9-c nodes. Thus, the Corrole-MOF-1 framework is classified as a 3D (3,9)-connected gfy net with the point symbol of $(4^{12}.6^{15}.8^9)(4^3)_3$ calculated using the TOPOS program (FIG. 1C). There have been very few (3,9)-c MOFs reported,[34] and Corrole-MOF-1 represents the first example of a zirconium MOF with (3,9)-c gfy topology.

Sample Activation and Gas Sorption Measurement. Before a gas sorption experiment, as-synthesized Corrole-MOF samples (~60 mg) were washed with DMF for three times and methanol for three times, followed by soaking in methanol for 72 h to allow solvent exchange. During the solvent exchange process, the methanol was decanted and replaced with fresh solvent for three times every 24 h. After that, the Corrole-MOF powders were isolated by centrifugation. Then, the resulting exchanged frameworks were activated by supercritical $CO_2$, prior to gas sorption measurement.

Figure 3A:
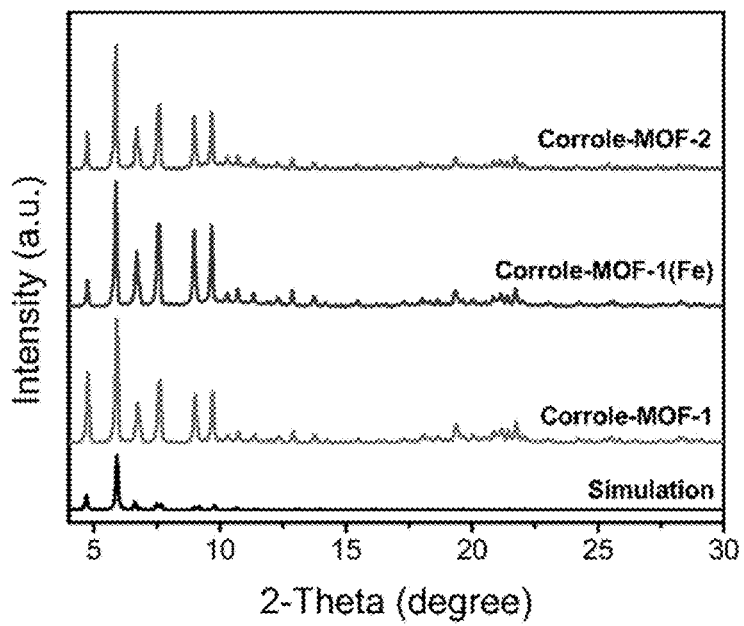
FIGS. 3A and 3B show (FIG. 3A) PXRD patterns and (FIG. 3B) N$_2$ sorption isotherms for Corrole-MOF-1, Corrole-MOF-1(Fe) and Corrole-MOF-2 at 77 K (inset shows pore size distributions).
Figure 3B:
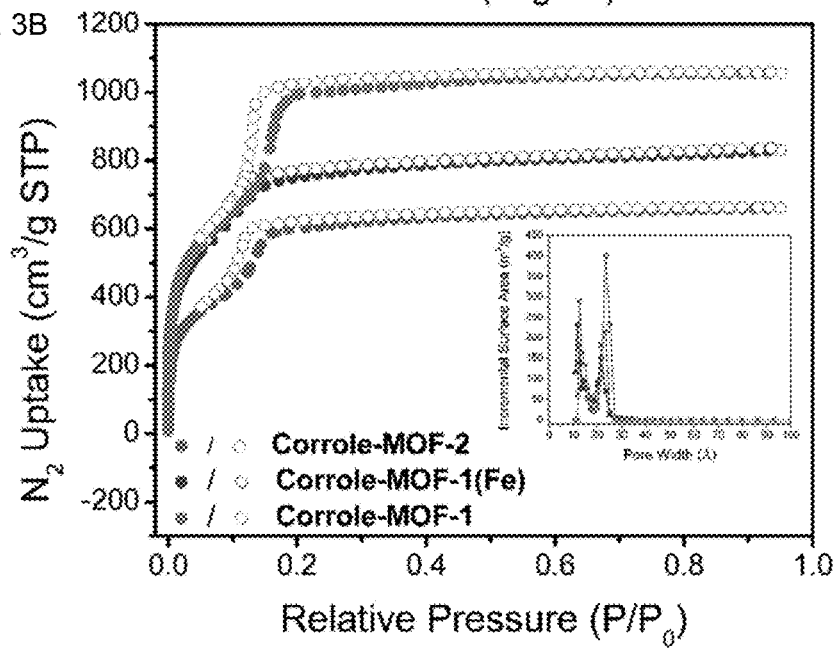

$N_2$ sorption isotherms were collected at 77 K to evaluate the porosity of Corrole-MOFs (FIG. 3B). The typical type IV isotherm of Corrole-MOF-1 shows a steep increase at $P/P_0$=0.15 with significant hysteresis loop, characteristic of mesoporous materials. Based on the $N_2$ adsorption data, a Brunauer-Emmett-Teller (BET) surface area of 2545 m$^2$ g$^{-1}$ and a total pore volume of 1.63 cm$^3$ g$^{-1}$ were calculated for Corrole-MOF-1 upon activation with acid aqueous solutions. The pore size distribution calculated by density functional theory (DFT) from the $N_2$ sorption curve indicates that the pores of Corrole-MOF-1 are predominantly distributed at 12.7 and 23.4 Å respectively being assigned to the microporous channels along a and b axes and the mesoporous hexagonal channels along c axis, which are consistent with the crystallographic data when the van der Waals contact is taken into account (FIGS. 1A-1G and 3B). The BET surface areas of Corrole-MOF-1(Fe) and Corrole-MOF-2 are 2145 m$^2$ g$^{-1}$ and 1662 m$^2$ g$^{-1}$, respectively as estimated from the $N_2$ sorption isotherms (FIG. 3B and Table 2). Thermogravimetric analyses indicated that the Corrole-MOFs are stable up to 350° C. under nitrogen atmosphere.

TABLE 2

BET Surface areas, Langmuir surface areas, mesopore sizes, $N_2$ uptakes, and total pore volumes for Corrole-MOF samples after treatment with pH = 2 aqueous solution.

| Corrole-MOF | BET surface area (m$^2$ g$^{-1}$) | Langmuir surface area (m$^2$ g$^{-1}$) | Mesopore size (Å)$^a$ | $N_2$ uptake (cm$^3$ g$^{-1}$ STP)$^b$ | Total pore volume (cm$^3$ g$^{-1}$)$^c$ |
|---|---|---|---|---|---|
| Corrole-MOF-1 | 2545 | 3343 | 23.4 | 1056 | 1.63 |
| Corrole-MOF-1(Fe) | 2145 | 2904 | 21.6 | 830 | 1.29 |
| Corrole-MOF-2 | 1662 | 2368 | 23.4 | 662 | 1.02 |

$^a$Calculated based on DFT method.
$^b$measurement was taken at $P/P_0$ = 0.95.
$^c$calculated by single point method.

Stability Test. For a solvent stability study, small amounts of freshly synthesized Corrole-MOF-1 (~10 mg) were added into different vials containing 3 mL of solvent or aqueous solution with a certain pH value. After 24 h, the samples were washed with fresh DMF twice for PXRD measurement or activated by supercritical $CO_2$ for $N_2$ adsorption test.

Figure 4A:
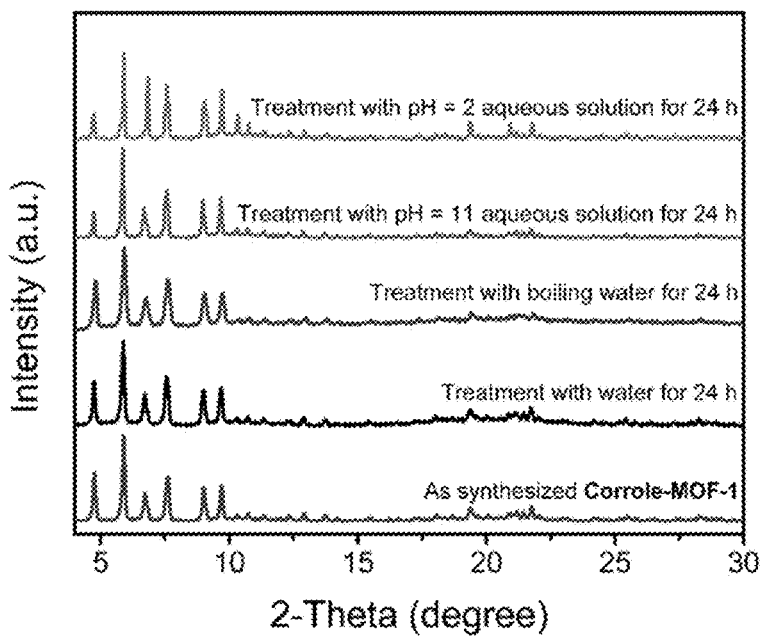
FIGS. 4A and 4B show (FIG. 4A) PXRD patterns and (FIG. 4B) N$_2$ sorption isotherms for Corrole-MOF-1 at 77 K, showing the framework stability upon treatment with water, boiling water, and aqueous solutions with pH values of 2 and 11.
Figure 4B:
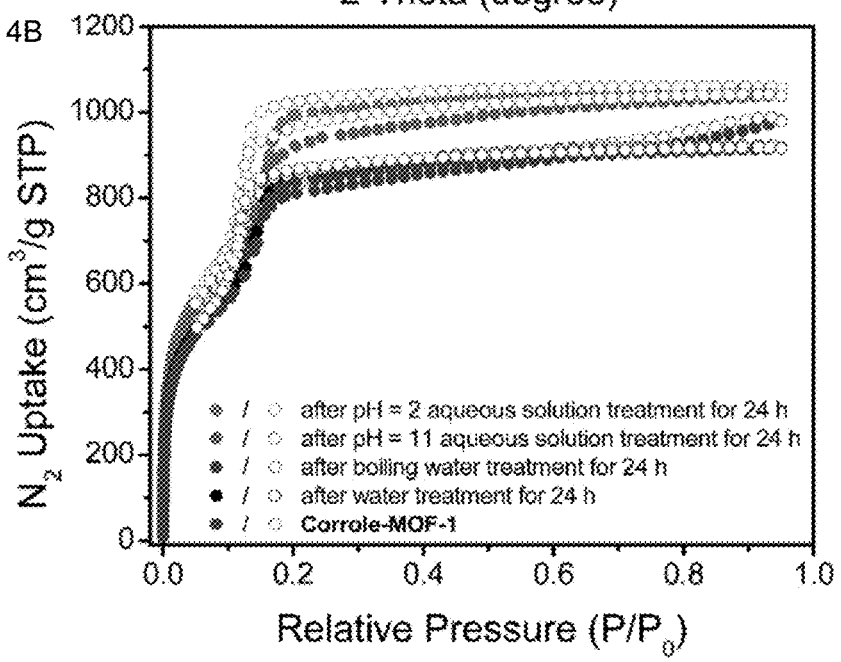

Corrole-MOF-1 demonstrates excellent chemical stability in various solvents and aqueous solutions of a wide pH range. After treatment under these various conditions, the PXRD patterns of Corrole-MOF-1 remain intact, suggesting the retention of crystallinity and structural integrity (FIG. 4A). To further investigate the stability of Corrole-MOF-1, $N_2$ sorption isotherms were measured after immersing samples in water, boiling water, as well as pH=2 and 11 aqueous solutions for 24 h. The $N_2$ uptakes of Corrole-MOF-1 after different treatments are comparable to that of the pristine sample, indicative of the robustness of the framework under harsh conditions (FIG. 4B and Table 3).

TABLE 3

BET Surface areas, Langmuir surface areas, mesopore sizes, $N_2$ uptakes and total pore volumes for Corrole-MOF-1 samples after treatments in diverse solutions for 24 h to show excellent stability.

| Treatments | BET surface area ($m^2\,g^{-1}$) | Langmuir surface area ($m^2\,g^{-1}$) | Mesopore size (Å)[a] | $N_2$ uptake ($cm^3\,g^{-1}$ STP)[b] | Total pore volume ($cm^3\,g^{-1}$)[c] |
|---|---|---|---|---|---|
| No treatment | 2206 | 3016 | 23.4 | 915 | 1.42 |
| Water | 2257 | 3078 | 23.4 | 918 | 1.42 |
| Boiling water | 2309 | 3269 | 23.4 | 980 | 1.52 |
| pH = 10 | 2466 | 3353 | 23.4 | 1039 | 1.61 |
| pH = 2 | 2545 | 3343 | 23.4 | 1056 | 1.63 |

[a]Calculated based on DFT method.
[b]measurement was taken at $P/P_0$ = 0.95.
[c]calculated by single point method.

Catalysis. An oven-dried Schlenk tube was charged with Corrole-MOF-1(Fe) (0.02 mmol) and $AgBF_4$ (0.1 mmol) under a dry nitrogen atomosphere in a glove box. Dry $CH_2Cl_2$ (2.0 mL) was added by syringe. The mixture was stirred for 3 h at room temperature. Then to the mixture, aldehyde (1.0 mmol), the diene (4.0 mmol) and dry toluene (6.0 mL) were added under the nitrogen protection in the glove box. The tube was sealed and heated to 80° C. After 24 h, the reactor was allowed to cool to room temperature and depressurized. The $^1H$ NMR analysis in conjugation with column chromatography isolation were employed to determine the conversion. The reaction solution was centrifuged to recover catalyst for the next cycle. The recovered MOF powders were washed by DMF and methanol and activated by supercritical $CO_2$. The structural stability of the framework after three recycles was confirmed by PXRD.

The employment of Corrole-MOFs as heterogeneous catalysts was examined in the context of investigating the Lewis acid catalytic activity of Corrole-MOF-1(Fe) for the [4+2] hetero-Diels-Alder (HDA) reaction between unactivated aldehydes and a simple diene. Meanwhile, the deactivation of catalyst via intermolecular pathways can also be well-restrained, which facilitates the catalytic processes. As expected, the integration of excellent chemical stability, large porosity and surface areas, and high density of catalytically active sites makes Corrole-MOF-1(Fe) an excellent heterogeneous catalyst for this reaction.

Notwithstanding, only a trace amount of product 3a was obtained when using Corrole-MOF-1(Fe) as the catalyst in the reaction of benzaldehyde (1a) with 2,3-dimethyl-1,3-butadiene (2), probably due to the presence of a strong axial coordinating chloride anion on the catalytic iron center blocking the catalytic process (Table 4, entry 2). To remedy this, the cationic catalyst [Corrole-MOF-1(Fe)]$BF_4$ was prepared by treating Corrole-MOF-1(Fe) with $AgBF_4$. The reaction of 1a with 2 in the presence of [Corrole-MOF-1(Fe)]$BF_4$ (2 mol %) in toluene at 80° C. for 24 h afforded dihydropyran 3a in 96% yield (93% isolated yield) as compared to only 67% yield in the presence of homogeneous ester-corrole catalyst Fe(TCMPC)$BF_4$ (Table 4, entries 5 and 6).

To further investigate the scope of corrole MOF-catalyzed HDA reactions, benzaldehydes bearing different electron-withdrawing and/or electron-donating substituents were tested. The dihydropyran products all formed in excellent yields compared to homogeneous systems (Table 4). It was found that both electronic and steric effects in the aldehydes could influence the reaction, in which strong electron-withdrawing substituents led to lower yield compared to electron-donating groups. Particularly, the lowest yield was resulted for the reaction of pentafluorobenzaldehyde (1e), while the reaction of p-tertbutylbenzaldehyde (1f) with 2 produced 3f in a moderate 77% yield, which is likely attributed to the steric effect of the large-sized tertbutyl substitute (Table 4, entries 16 and 18). When compared with [Corrole-MOF-1(Fe)]$BF_4$, the porphyrinic MOF PCN-224 (Fe)$BF_4$ catalyzed HDA reactions of aldehydes (1b, 1c and 1g) with 2 resulted in the lower yields of the desired dihydropyran products 3 (Table 4, entries 12 and 21). Owing to the high stability of Corrole-MOFs, [Corrole-MOF-1(Fe)]$BF_4$ can be recycled and maintain high catalytic activity after three cycles, with retention of structural integrity as suggested by PXRD patterns (Table 4, entry 24).

TABLE 4

Hetero-Diels-Alder reaction of aldehydes with 2,3-dimethyl-1,3-butadiene.

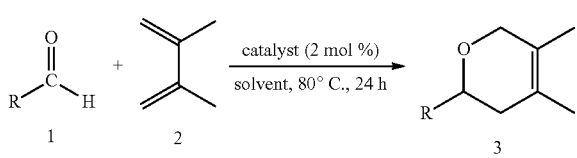

| entry[a] | catalyst | R | solvent | product | yield (%)[b] | TON[g] | TOF ($h^{-1}$)[h] |
|---|---|---|---|---|---|---|---|
| 1 | Corrole-MOF-1 | Ph | toluene | 3a | <1 | — | — |
| 2 | Corrole-MOF-1(Fe) | Ph | toluene | 3a | <1 | — | — |

TABLE 4-continued

Hetero-Diels-Alder reaction of aldehydes with 2,3-dimethyl-1,3-butadiene.

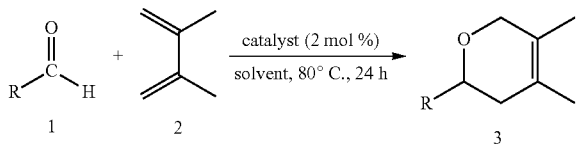

| entry[a] | catalyst | R | solvent | product | yield (%)[b] | TON[g] | TOF (h$^{-1}$)[h] |
|---|---|---|---|---|---|---|---|
| 3 | AgBF$_4$ | Ph | toluene | 3a | <1 | — | — |
| 4[c] | Fe(TCPC)BF$_4$ | Ph | THF | 3a | <1 | — | — |
| 5[d] | Fe(TCMPC)BF$_4$ | Ph | toluene | 3a | 67 | 33.5 | 1.40 |
| 6 | [Corrole-MOF-1(Fe)]BF$_4$ | Ph | toluene | 3a | 96 (93) | 48.0 | 2.00 |
| 7 | Fe(TCMPC)BF$_4$ | 4-Br—Ph | toluene | 3b | 62 | 31.0 | 1.30 |
| 8 | [Corrole-MOF-1(Fe)]BF$_4$ | 4-Br—Ph | toluene | 3b | 95 (92) | 47.5 | 1.98 |
| 9[e] | PCN-224(Fe)BF$_4$ | 4-Br—Ph | toluene | 3b | 87 (83) | 43.5 | 1.81 |
| 10 | Fe(TCMPC)BF$_4$ | 4-CN—Ph | toluene | 3c | 65 | 32.5 | 1.35 |
| 11 | [Corrole-MOF-1(Fe)]BF$_4$ | 4-CN—Ph | toluene | 3c | 91 (87) | 45.5 | 1.90 |
| 12[e] | PCN-224(Fe)BF$_4$ | 4-CN—Ph | toluene | 3c | 83 (78) | 41.5 | 1.73 |
| 13 | Fe(TCMPC)BF$_4$ | 4-NO$_2$—Ph | toluene | 3d | 60 | 30.0 | 1.25 |
| 14 | [Corrole-MOF-1(Fe)]BF$_4$ | 4-NO$_2$—Ph | toluene | 3d | 84 (81) | 42.0 | 1.75 |
| 15 | Fe(TCMPC)BF$_4$ | 5F—Ph | toluene | 3e | 56 | 28.0 | 1.17 |
| 16 | [Corrole-MOF-1(Fe)]BF$_4$ | 5F—Ph | toluene | 3e | 77 (73) | 38.5 | 1.60 |
| 17 | Fe(TCMPC)BF$_4$ | 4-C(CH$_3$)$_3$—Ph | toluene | 3f | 71 | 35.5 | 1.48 |
| 18 | [Corrole-MOF-1(Fe)]BF$_4$ | 4-C(CH$_3$)$_3$—Ph | toluene | 3f | 82 (77) | 41.0 | 1.71 |
| 19 | Fe(TCMPC)BF$_4$ | 4-OMe—Ph | toluene | 3g | 78 | 39.0 | 1.63 |
| 20 | [Corrole-MOF-1(Fe)]BF$_4$ | 4-OMe—Ph | toluene | 3g | 97 (94) | 48.5 | 2.02 |
| 21[e] | PCN-224(Fe)BF$_4$ | 4-OMe—Ph | toluene | 3g | 86 (82) | 43.0 | 1.79 |
| 22 | Fe(TCMPC)BF$_4$ | 3-Br-4-OMe—Ph | toluene | 3h | 73 | 36.5 | 1.52 |
| 23 | [Corrole-MOF-1(Fe)]BF$_4$ | 3-Br-4-OMe—Ph | toluene | 3h | 93 (89) | 46.5 | 1.94 |
| 24[f] | [Corrole-MOF-1(Fe)]BF$_4$ | Ph | toluene | 3a | 90 (87) | 45.0 | 1.88 |

[a]Reaction conditions: catalyst (2 mol %), aldehyde (1.0 mmol), and diene (3.0 mmol) in 6.0 ml THF or toluene at 80° C.
[b]Calculated by $^1$H NMR with mesitylene as the internal standard, isolated yields in parentheses.
[c]Carboxylate corrole ligand catalyzing HDA reaction in THF.
[d]Ester-corrole as the homogeneous catalyst.
[e]Porphyrinic MOF PCN-224(Fe) served as compared heterogeneous catalyst.
[f]After 3$^{rd}$ catalyst recycles.
[g]TON = turnover number.
[h]TOF = turnover frequency.
The calculations of TON and TOF are based on the yield determined by $^1$H NMR.

Preparation and Evaluation of Organic Frameworks

Synthesis of 5,10,15-tris(p-nitrophenyl)corrole (H$_3$TPNPC). p-Nitrobenzaldehyde (1 equiv, 10 mmol, 1.51 g) and pyrrole (2 equiv, 20 mmol, 1.39 ml) were dissolved in MeOH (400 ml) previously loaded into 1000 mL round-bottom flask, and H$_2$O (400 ml) was added. Subsequently, 8.5 ml of 36% HCl aqueous solution was added and the reaction was stirred at room temperature for 3 h. The mixture was extracted with CH$_2$Cl$_2$, and the organic layer was washed with H$_2$O, dried with MgSO$_4$, filtered, and diluted to 600 ml CH$_2$Cl$_2$. Tetrachloro-p-benzoquinone (1 equiv, 10 mmol, 2.46 g) was added, and the mixture was refluxed for 2 h. Then the reaction mixture without concentration was passed over a chromatography column (silica gel, eluent: CH$_2$Cl$_2$). All fractions containing corrole were collected and evaporated to dryness. The residue was washed with methanol to give the pure corrole (308 mg, 14%). ESI-MS (positive mode) m/z: 662.1751 [M+H]$^+$. $^1$H NMR (CDCl$_3$, 400 MHz): δ9.15; (d, 2H, J=4.0 Hz), 8.94; (d, 2H, J=4.3 Hz), 8.73; (d, 4H, J=8.0 Hz), 8.69; (b, 4H), 8.59; (d, 2H, J=4.7 Hz), 8.54; (d, 4H, J=8.3 Hz), 8.40; (d, 2H, J=8.7 Hz). UVNis (CHCl$_3$): λmax: 448, 595 nm.

TABLE 5

Crystal data and structure refinement for H$_3$TPNPC.

| Identification code | H$_3$TPNPC |
|---|---|
| CCDC number | 1939970 |
| Empirical formula | C$_{38.48}$H$_{24.48}$Cl$_{4.72}$N$_7$O$_6$ |
| Moiety formula | C$_{37}$H$_{23}$N$_7$O$_6$·solv |
| Formula weight | 848.12 |
| Temperature/K | 100.0 |
| Crystal system | triclinic |
| Space group | P-1 |
| a/Å | 16.7868(5) |
| b/Å | 16.8396(4) |
| c/Å | 17.7319(5) |
| α/° | 62.8930(10) |
| β/° | 62.8070(10) |
| γ/° | 65.4090(10) |
| Volume/Å$^3$ | 3829.48(19) |
| Z | 4 |
| ρ$_{calc}$g/cm$^3$ | 1.471 |
| μ/mm$^{-1}$ | 3.755 |
| F(000) | 1730.0 |
| Crystal size/mm$^3$ | 0.263 × 0.084 × 0.058 |
| Radiation | CuKα (λ = 1.54178) |
| 2Θ range for data collection/° | 5.932 to 160.05 |
| Index ranges | −21 ≤ h ≤ 21, −21 ≤ k ≤ 21, −22 ≤ l ≤ 21 |
| Reflections collected | 96216 |
| Independent reflections | 16278 [R$_{int}$ = 0.0437, R$_{sigma}$ = 0.0251] |
| Data/restraints/parameters | 16278/725/1322 |

TABLE 5-continued

Crystal data and structure refinement for H₃TPNPC.

| Identification code | H₃TPNPC |
|---|---|
| Goodness-of-fit on $F^2$ | 1.054 |
| Final R indexes [I >= 2σ (I)] | $R_1$ = 0.0775, $wR_2$ = 0.2138 |
| Final R indexes [all data] | $R_1$ = 0.0879, $wR_2$ = 0.2273 |
| Largest diff. peak/hole/e Å$^{-3}$ | 0.97/−1.03 |

H₃TPNPC: Heavily disordered chloroform molecules were refined using restraints and occupancy was refined using free variables (FVAR). Some of chloroform molecules could be located only partially and in this case only Cl atoms were included in the model. The total number of chloroform molecules is tentative.

Synthesis of 5,10,15-tris(p-aminophenyl)corrole (H₃TPAPC). A solution of 315 mg (1 equiv, 0.48 mmol) of H₃TPNPC and 1075 mg (10 equiv, 4.8 mmol) of SnCl₂.2H₂O in 30 ml of 36% HCl was bubbled with N₂ for 15 minutes, and then, which was stirred and heated in an oil bath (75° C.) for 1.5 h. The reaction mixture was cooled down to the room temperature and added in the ice water, which was neutralized by slow addition of concentrated NH₄OH until pH≥8. The resulting solution was extracted with EtOAc, dried over NaSO₄ and evaporated under reduced pressure. The crude product was purified by column chromatography (silica gel, CH₂Cl₂/EtOAc/TEA=50/50/1) to afford the pure corrole in 32% yield (86 mg). ESI-MS (positive mode) m/z: 572.2569 [M+H]⁺. ¹H NMR (CDCl₃, 400 MHz): δ 8.91; (br, 4H), 8.58; (br, 4H), 8.20; (d, 4H, J=7.5 Hz), 7.97; (d, 2H, J=7.8 Hz) 7.15; (d, 4H, J=7.6 Hz), 7.08; (d, 2H, J=7.5 Hz). UVNis (CHCl₃): $\lambda_{max}$: 405, 426, 529, 590, 631, 662 nm.

Synthesis of TPAPC-COF. A Pyrex tube measuring o.d.xi.d.=9.5×7.5 mm² was charged with H₃TPAPC (11.4 mg, 0.02 mmol) and terephthalaldehyde (TA) (4.0 mg, 0.03 mmol) in a mixed solution of n-butylalcohol (1.0 ml), mesitylene (0.5 ml), and 6 M aqueous acetic acid (0.1 ml). The tube was flash frozen at 77 K (liquid N₂ bath), evacuated, and flame-sealed. Upon sealing, the length of the tube was reduced to ca. 15 cm. The reaction mixture was heated at 120° C. for 3 days to afford a dark precipitate which was isolated by filtration and washed by Soxhlet extraction in THF and acetone for 24 h, respectively. The product was dried under vacuum at 80° C. for 12 h to afford dark powder in 86% isolated yield. Elemental analysis: Calcd. for $C_{49}H_{29}N_7$: C (82.23%), H (4.06%), N (13.71%). Found: C (80.76%), H (4.93%), N (14.31%).

Chemical Stability of TPAPC-COF. For various solvents and acid or base stability study, small amounts of prepared TPAPC-COF (10 mg) were immersed into different vials containing 10 mL of solutions for 72 h. After that, samples were isolated by centrifugation, and washed with THF and acetone and dried to measure PXRD patterns. Thermogravimetric analysis (TGA) showed that TPAPC-COF is stable up to 400° C. in nitrogen atmosphere.

Gas Sorption Experiments of TPAPC-COF. Before measurement, the samples were degassed in vacuum at 120° C. and 1×10⁻⁵ torr for 10 h. For N₂ sorption isotherm measurements, a liquid N₂ bath was used for adsorption measurement at 77 K. The Brunauer-Emmett-Teller (BET) method was utilized to calculate the surface area. The pore size distribution curves of TPAPC-COF was obtained via the nonlocal density functional theory (NLDFT) based on a carbon model containing slit pores.

The permanent porosity of TPAPC-COF was investigated by measuring N₂ sorption isotherms at 77 K on the freshly activated samples. Through screening the different reaction solvent systems and ratios, the highest BET surface area of TPAPC-COF was obtained by using the mixed solvents of n butanol/mesitylene/acetic acid (10:5:1, by vol.). As displayed in FIG. 7C, TPAPC-COF exhibited the typical type-I isotherm with a sharp uptake at the low relative pressure (PIP₀<0.1), which is a significant feature of microporous materials. The BET model was applied to the isotherm of TPAPC-COF for PIP₀ between 10⁻⁴ and 0.1 to afford BET surface area of 745 m²/g, and the corresponding total pore volume calculated at PIP₀=0.95 is 0.44 cm³/g. Nonlocal density functional theory (NLDFT) fitting of the adsorption branch for TPAPC-COF displays the pore size distributions (10 to 20 Å).

Structural Simulation of TPAPC-COF. The structure model of TPAPC-COF was generated with the Materials Studio programs. The initial unit cell dimension was set to the theoretical parameters. The Le Bail refinement was performed to optimize the lattice parameters iteratively until the $R_{wp}$ value converges and the overlay of the observed with refined profiles shows good agreement. The atomic positions and total energies were then fully optimized using Forcite module of Materials Studio. The final crystal structure was then optimized using the Castep module of Materials Studio. The fractional atomistic coordinates for crystal structure of TPAPC-COF are provided in Table 6.

TABLE 6

Fractional atomistic coordinates for crystal structure of TPAPC-COF.
TPAPC-COF
Space group: P1
a = 52.2892 Å, b = 40.7693 Å, c = 8.8687 Å
α = 95.604°, β = 104.523°, γ = 129.098°
$R_{wp}$ = 3.23%, $R_p$ = 2.27%

| Atom | a/x | b/y | c/z |
|---|---|---|---|
| C1 | 0.4165 | 0.8425 | 0.2325 |
| C2 | 0.4097 | 0.8067 | 0.13 |
| C3 | 0.3857 | 0.7629 | 0.1313 |
| C4 | 0.3674 | 0.7514 | 0.2381 |
| C5 | 0.3744 | 0.7874 | 0.3406 |
| C6 | 0.398 | 0.8314 | 0.3378 |
| C7 | 0.3949 | 0.7062 | 0.2913 |
| C8 | 0.3577 | 0.6834 | 0.2492 |
| N9 | 0.3404 | 0.6386 | 0.2269 |
| C10 | 0.3642 | 0.6317 | 0.2515 |
| C11 | 0.2643 | 0.4861 | 0.1942 |
| C12 | 0.2974 | 0.5061 | 0.1865 |
| C13 | 0.3202 | 0.5535 | 0.2462 |
| N14 | 0.3001 | 0.5607 | 0.2908 |
| C15 | 0.2659 | 0.5208 | 0.259 |
| C16 | 0.3553 | 0.5902 | 0.2494 |
| C17 | 0.1919 | 0.5139 | 0.2665 |
| C18 | 0.2042 | 0.4919 | 0.265 |
| C19 | 0.2393 | 0.5223 | 0.267 |
| N20 | 0.2469 | 0.5613 | 0.2704 |
| C21 | 0.2189 | 0.5582 | 0.2657 |
| C22 | 0.2919 | 0.7029 | 0.2173 |
| C23 | 0.259 | 0.6739 | 0.2249 |
| C24 | 0.2529 | 0.6351 | 0.2503 |
| N25 | 0.2834 | 0.6425 | 0.2571 |
| C26 | 0.3076 | 0.6832 | 0.2389 |
| C27 | 0.3427 | 0.7035 | 0.2416 |
| C28 | 0.221 | 0.5952 | 0.2575 |
| C29 | 0.3987 | 0.6755 | 0.292 |
| C30 | 0.3797 | 0.5813 | 0.2495 |
| C31 | 0.1882 | 0.5881 | 0.2546 |
| C32 | 0.404 | 0.599 | 0.1706 |
| C33 | 0.4235 | 0.5866 | 0.1629 |
| C34 | 0.4212 | 0.556 | 0.2372 |
| C35 | 0.3976 | 0.5389 | 0.3196 |

TABLE 6-continued

Fractional atomistic coordinates for crystal structure of TPAPC-COF.
TPAPC-COF
Space group: P1
a = 52.2892 Å, b = 40.7693 Å, c = 8.8687 Å
α = 95.604°, β = 104.523°, γ = 129.098°
$R_{wp}$ = 3.23%, $R_p$ = 2.27%

| Atom | a/x | b/y | c/z |
|---|---|---|---|
| C36 | 0.378 | 0.5512 | 0.3253 |
| C37 | 0.1522 | 0.5469 | 0.1576 |
| C38 | 0.1217 | 0.5377 | 0.1624 |
| C39 | 0.1244 | 0.5696 | 0.2652 |
| C40 | 0.1602 | 0.6113 | 0.3585 |
| C41 | 0.1906 | 0.62 | 0.3544 |
| H42 | 0.4409 | 0.6011 | 0.0963 |
| H43 | 0.4072 | 0.6223 | 0.1079 |
| H44 | 0.3607 | 0.5366 | 0.3926 |
| H45 | 0.3942 | 0.5152 | 0.38 |
| H46 | 0.3039 | 0.4883 | 0.1353 |
| H47 | 0.241 | 0.4505 | 0.1523 |
| H48 | 0.4238 | 0.6833 | 0.3244 |
| H49 | 0.4167 | 0.742 | 0.3238 |
| H50 | 0.381 | 0.7367 | 0.0469 |
| H51 | 0.423 | 0.8133 | 0.0452 |
| H52 | 0.4028 | 0.8576 | 0.423 |
| H53 | 0.3618 | 0.7812 | 0.4282 |
| H54 | 0.3037 | 0.7343 | 0.195 |
| H55 | 0.2403 | 0.6784 | 0.2109 |
| H56 | 0.2171 | 0.6527 | 0.4334 |
| H57 | 0.1646 | 0.6377 | 0.4401 |
| H58 | 0.1476 | 0.5209 | 0.0717 |
| H59 | 0.0953 | 0.5054 | 0.0807 |
| H60 | 0.1661 | 0.4996 | 0.268 |
| H61 | 0.1897 | 0.4578 | 0.264 |
| H62 | 0.3131 | 0.6137 | 0.1712 |
| C63 | 0.5772 | 0.1734 | 0.2211 |
| C64 | 0.5686 | 0.1875 | 0.0941 |
| C65 | 0.5929 | 0.232 | 0.0984 |
| C66 | 0.6269 | 0.2659 | 0.2317 |
| C67 | 0.6354 | 0.2515 | 0.3572 |
| C68 | 0.6116 | 0.2067 | 0.3525 |
| C69 | 0.6002 | 0.3126 | 0.2112 |
| C70 | 0.6367 | 0.3348 | 0.236 |
| N71 | 0.6533 | 0.379 | 0.2491 |
| C72 | 0.6295 | 0.3858 | 0.2308 |
| C73 | 0.7293 | 0.5306 | 0.2932 |
| C74 | 0.6959 | 0.5107 | 0.2972 |
| C75 | 0.6726 | 0.4633 | 0.2292 |
| N76 | 0.6924 | 0.4561 | 0.1808 |
| C77 | 0.7272 | 0.4959 | 0.2212 |
| C78 | 0.6376 | 0.4266 | 0.2285 |
| C79 | 0.8054 | 0.508 | 0.2684 |
| C80 | 0.7921 | 0.5289 | 0.2664 |
| C81 | 0.7543 | 0.4951 | 0.2183 |
| N82 | 0.7459 | 0.455 | 0.1889 |
| C83 | 0.776 | 0.4608 | 0.2237 |
| C84 | 0.6998 | 0.3128 | 0.2347 |
| C85 | 0.7332 | 0.342 | 0.2317 |
| C86 | 0.7424 | 0.3842 | 0.2384 |
| N87 | 0.7136 | 0.379 | 0.2475 |
| C88 | 0.6873 | 0.3361 | 0.2447 |
| C89 | 0.652 | 0.3153 | 0.2406 |
| C90 | 0.7743 | 0.4241 | 0.2311 |
| C91 | 0.5959 | 0.3427 | 0.2069 |
| C92 | 0.6133 | 0.4355 | 0.2297 |
| C93 | 0.8073 | 0.4322 | 0.2341 |
| C94 | 0.6149 | 0.4656 | 0.1539 |
| C95 | 0.5952 | 0.4776 | 0.1591 |
| C96 | 0.5713 | 0.4602 | 0.2405 |
| C97 | 0.5691 | 0.4297 | 0.3151 |
| C98 | 0.5889 | 0.4177 | 0.3084 |
| C99 | 0.8273 | 0.4581 | 0.1446 |
| C100 | 0.8589 | 0.4687 | 0.1485 |
| C101 | 0.8734 | 0.4538 | 0.243 |
| C102 | 0.8531 | 0.427 | 0.3296 |
| C103 | 0.822 | 0.4172 | 0.3271 |
| H104 | 0.5986 | 0.5014 | 0.0992 |
| H105 | 0.6323 | 0.4803 | 0.0875 |
| H106 | 0.5859 | 0.3946 | 0.3718 |
| H107 | 0.5516 | 0.415 | 0.3812 |
| H108 | 0.6896 | 0.5282 | 0.3516 |
| H109 | 0.7531 | 0.5661 | 0.3412 |
| H110 | 0.5711 | 0.3349 | 0.1852 |
| H111 | 0.5792 | 0.2776 | 0.1963 |
| H112 | 0.5849 | 0.2405 | −0.0047 |
| H113 | 0.5427 | 0.1631 | −0.0114 |
| H114 | 0.6195 | 0.1981 | 0.4555 |
| H115 | 0.6612 | 0.2759 | 0.4636 |
| H116 | 0.6851 | 0.2782 | 0.2288 |
| H117 | 0.7494 | 0.3346 | 0.2214 |
| H118 | 0.8089 | 0.3975 | 0.4017 |
| H119 | 0.8626 | 0.4143 | 0.4056 |
| H120 | 0.8177 | 0.4701 | 0.0656 |
| H121 | 0.8719 | 0.4881 | 0.0731 |
| H122 | 0.8334 | 0.525 | 0.3065 |
| H123 | 0.8078 | 0.5646 | 0.2983 |
| H124 | 0.6806 | 0.4039 | 0.2953 |
| C125 | 0.4801 | 0.5264 | 0.2618 |
| C126 | 0.4613 | 0.4862 | 0.1329 |
| C127 | 0.4769 | 0.4688 | 0.1129 |
| C128 | 0.5122 | 0.4894 | 0.2188 |
| C129 | 0.5309 | 0.5295 | 0.3482 |
| C130 | 0.5153 | 0.5469 | 0.368 |
| N131 | 0.5561 | 0.4786 | 0.2708 |
| C132 | 0.5264 | 0.4677 | 0.1821 |
| C133 | 0.4658 | 0.5481 | 0.2974 |
| N134 | 0.4363 | 0.5375 | 0.2073 |
| C135 | 0.4341 | 0.468 | 0.0458 |
| H136 | 0.4609 | 0.4377 | 0.0102 |
| H137 | 0.5581 | 0.5475 | 0.4356 |
| H138 | 0.5314 | 0.5779 | 0.4707 |
| H139 | 0.5074 | 0.4391 | 0.0622 |
| H140 | 0.4848 | 0.5766 | 0.4178 |
| C141 | 0.4711 | 0.9642 | 0.2424 |
| C142 | 0.5057 | 0.9826 | 0.2591 |
| C143 | 0.5317 | 0.0265 | 0.2614 |
| C144 | 0.525 | 0.0549 | 0.2459 |
| C145 | 0.4903 | 0.0364 | 0.2292 |
| C146 | 0.4644 | 0.9927 | 0.2283 |
| N147 | 0.5498 | 0.1287 | 0.2185 |
| C148 | 0.5539 | 0.1014 | 0.2475 |
| C149 | 0.4419 | 0.9174 | 0.238 |
| N150 | 0.4439 | 0.8872 | 0.2358 |
| H151 | 0.5124 | 0.9623 | 0.2706 |
| H152 | 0.558 | 0.0392 | 0.2748 |
| H153 | 0.4836 | 0.0567 | 0.2171 |
| H154 | 0.4381 | 0.9801 | 0.2154 |
| H155 | 0.5801 | 0.1107 | 0.2715 |
| H156 | 0.417 | 0.9097 | 0.2314 |
| C157 | 0.0306 | 0.5207 | 0.2457 |
| C158 | 0.0304 | 0.5551 | 0.2843 |
| C159 | 0.9996 | 0.5458 | 0.2844 |
| C160 | 0.9662 | 0.5019 | 0.2475 |
| C161 | 0.9664 | 0.4675 | 0.2087 |
| C162 | −0.0028 | 0.4768 | 0.2081 |
| N163 | 0.9035 | 0.4594 | 0.2402 |
| C164 | 0.9346 | 0.4959 | 0.2521 |
| C165 | 0.0624 | 0.5269 | 0.2427 |
| N166 | 0.0947 | 0.5645 | 0.2715 |
| H167 | 0.0549 | 0.5899 | 0.3155 |
| H168 | 1.0016 | 0.5742 | 0.3157 |
| H169 | 0.9419 | 0.4327 | 0.1777 |
| H170 | −0.0049 | 0.4484 | 0.1766 |
| H171 | 0.9411 | 0.5283 | 0.2738 |
| H172 | 0.0554 | 0.4942 | 0.2135 |
| C173 | 0.9199 | 0.8423 | 0.7366 |
| C174 | 0.9131 | 0.8066 | 0.6342 |
| C175 | 0.889 | 0.7627 | 0.6353 |
| C176 | 0.8707 | 0.7512 | 0.7417 |
| C177 | 0.8776 | 0.7871 | 0.8441 |

TABLE 6-continued

Fractional atomistic coordinates for crystal structure of TPAPC-COF.
TPAPC-COF
Space group: P1
a = 52.2892 Å, b = 40.7693 Å, c = 8.8687 Å
α = 95.604°, β = 104.523°, γ = 129.098°
$R_{wp}$ = 3.23%, $R_p$ = 2.27%

| Atom | a/x | b/y | c/z |
|---|---|---|---|
| C178 | 0.9012 | 0.8311 | 0.8416 |
| C179 | 0.8981 | 0.7059 | 0.7948 |
| C180 | 0.861 | 0.6831 | 0.7523 |
| N181 | 0.8436 | 0.6383 | 0.7295 |
| C182 | 0.8674 | 0.6314 | 0.754 |
| C183 | 0.7673 | 0.4857 | 0.6942 |
| C184 | 0.8005 | 0.5057 | 0.6871 |
| C185 | 0.8233 | 0.5531 | 0.7476 |
| N186 | 0.8032 | 0.5602 | 0.7922 |
| C187 | 0.7689 | 0.5203 | 0.7596 |
| C188 | 0.8585 | 0.5898 | 0.7513 |
| C189 | 0.6948 | 0.5133 | 0.7664 |
| C190 | 0.7071 | 0.4913 | 0.7646 |
| C191 | 0.7423 | 0.5218 | 0.7674 |
| N192 | 0.7499 | 0.5608 | 0.7716 |
| C193 | 0.7219 | 0.5577 | 0.7666 |
| C194 | 0.7951 | 0.7026 | 0.7206 |
| C195 | 0.7622 | 0.6735 | 0.7277 |
| C196 | 0.7561 | 0.6347 | 0.7524 |
| N197 | 0.7866 | 0.6421 | 0.7593 |
| C198 | 0.8108 | 0.6829 | 0.7418 |
| C199 | 0.846 | 0.7033 | 0.7448 |
| C200 | 0.7241 | 0.5947 | 0.759 |
| C201 | 0.9019 | 0.6752 | 0.795 |
| C202 | 0.8828 | 0.5809 | 0.7509 |
| C203 | 0.6913 | 0.5876 | 0.7558 |
| C204 | 0.9071 | 0.5987 | 0.6721 |
| C205 | 0.9266 | 0.5863 | 0.6637 |
| C206 | 0.9242 | 0.5555 | 0.7372 |
| C207 | 0.9006 | 0.5384 | 0.8196 |
| C208 | 0.8811 | 0.5507 | 0.826 |
| C209 | 0.6553 | 0.5465 | 0.6582 |
| C210 | 0.6248 | 0.5373 | 0.6626 |
| C211 | 0.6274 | 0.5691 | 0.7659 |
| C212 | 0.6633 | 0.6108 | 0.8599 |
| C213 | 0.6937 | 0.6195 | 0.856 |
| H214 | 0.944 | 0.6009 | 0.5972 |
| H215 | 0.9104 | 0.6221 | 0.61 |
| H216 | 0.8638 | 0.536 | 0.8932 |
| H217 | 0.8971 | 0.5145 | 0.8794 |
| H218 | 0.807 | 0.488 | 0.6356 |
| H219 | 0.744 | 0.45 | 0.6515 |
| H220 | 0.927 | 0.683 | 0.8275 |
| H221 | 0.92 | 0.7418 | 0.8276 |
| H222 | 0.8845 | 0.7366 | 0.5509 |
| H223 | 0.9264 | 0.8132 | 0.5497 |
| H224 | 0.906 | 0.8574 | 0.9267 |
| H225 | 0.865 | 0.7809 | 0.9315 |
| H226 | 0.807 | 0.7341 | 0.6988 |
| H227 | 0.7435 | 0.6781 | 0.7139 |
| H228 | 0.7201 | 0.6521 | 0.9357 |
| H229 | 0.6676 | 0.6371 | 0.9419 |
| H230 | 0.6506 | 0.5205 | 0.5719 |
| H231 | 0.5983 | 0.5051 | 0.5806 |
| H232 | 0.669 | 0.4989 | 0.7674 |
| H233 | 0.6926 | 0.4571 | 0.7629 |
| H234 | 0.8163 | 0.6134 | 0.6736 |
| C235 | 0.0804 | 0.1731 | 0.7248 |
| C236 | 0.0718 | 0.1873 | 0.598 |
| C237 | 0.0959 | 0.2317 | 0.6019 |
| C238 | 0.1301 | 0.2656 | 0.7346 |
| C239 | 0.1388 | 0.2512 | 0.8598 |
| C240 | 0.115 | 0.2065 | 0.8556 |
| C241 | 0.1034 | 0.3123 | 0.7142 |
| C242 | 0.1398 | 0.3345 | 0.7384 |
| N243 | 0.1564 | 0.3786 | 0.7507 |
| C244 | 0.1326 | 0.3854 | 0.7324 |
| C245 | 0.2321 | 0.53 | 0.791 |
| C246 | 0.1987 | 0.5101 | 0.7951 |
| C247 | 0.1755 | 0.4627 | 0.7286 |
| N248 | 0.1953 | 0.4555 | 0.6811 |
| C249 | 0.2301 | 0.4953 | 0.7205 |
| C250 | 0.1406 | 0.4262 | 0.7289 |
| C251 | 0.3083 | 0.5074 | 0.7684 |
| C252 | 0.295 | 0.5283 | 0.7659 |
| C253 | 0.2572 | 0.4945 | 0.718 |
| N254 | 0.2489 | 0.4545 | 0.6894 |
| C255 | 0.2789 | 0.4603 | 0.7243 |
| C256 | 0.2029 | 0.3123 | 0.7361 |
| C257 | 0.2362 | 0.3415 | 0.7327 |
| C258 | 0.2454 | 0.3838 | 0.7396 |
| N259 | 0.2167 | 0.3786 | 0.7492 |
| C260 | 0.1904 | 0.3358 | 0.7466 |
| C261 | 0.1551 | 0.3149 | 0.743 |
| C262 | 0.2773 | 0.4236 | 0.732 |
| C263 | 0.0991 | 0.3424 | 0.7095 |
| C264 | 0.1163 | 0.4349 | 0.7297 |
| C265 | 0.3103 | 0.4317 | 0.7345 |
| C266 | 0.1174 | 0.4645 | 0.6516 |
| C267 | 0.0976 | 0.4764 | 0.6561 |
| C268 | 0.0742 | 0.4595 | 0.7394 |
| C269 | 0.0724 | 0.4296 | 0.8166 |
| C270 | 0.0922 | 0.4176 | 0.8103 |
| C271 | 0.3303 | 0.4576 | 0.6451 |
| C272 | 0.3618 | 0.4681 | 0.6487 |
| C273 | 0.3763 | 0.4532 | 0.7427 |
| C274 | 0.356 | 0.4263 | 0.8293 |
| C275 | 0.3249 | 0.4166 | 0.8271 |
| H276 | 0.1007 | 0.4997 | 0.5943 |
| H277 | 0.1346 | 0.4789 | 0.5837 |
| H278 | 0.0895 | 0.395 | 0.8755 |
| H279 | 0.0552 | 0.4154 | 0.8844 |
| H280 | 0.1923 | 0.5277 | 0.8483 |
| H281 | 0.2558 | 0.5656 | 0.8378 |
| H282 | 0.0743 | 0.3347 | 0.6882 |
| H283 | 0.0825 | 0.2774 | 0.7001 |
| H284 | 0.0879 | 0.2401 | 0.499 |
| H285 | 0.0458 | 0.1628 | 0.493 |
| H286 | 0.123 | 0.1979 | 0.9584 |
| H287 | 0.1646 | 0.2757 | 0.9658 |
| H288 | 0.1881 | 0.2778 | 0.7301 |
| H289 | 0.2523 | 0.3341 | 0.7219 |
| H290 | 0.3119 | 0.3969 | 0.9017 |
| H291 | 0.3654 | 0.4136 | 0.9049 |
| H292 | 0.3206 | 0.4696 | 0.5664 |
| H293 | 0.3748 | 0.4876 | 0.5733 |
| H294 | 0.3364 | 0.5245 | 0.8066 |
| H295 | 0.3107 | 0.564 | 0.7973 |
| H296 | 0.1837 | 0.4035 | 0.7964 |
| C297 | 0.9829 | 0.5257 | 0.76 |
| C298 | 0.9643 | 0.4857 | 0.6299 |
| C299 | 0.9798 | 0.4683 | 0.6098 |
| C300 | 0.015 | 0.4887 | 0.7163 |
| C301 | 0.0336 | 0.5286 | 0.8465 |
| C302 | 0.0181 | 0.546 | 0.8667 |
| N303 | 0.0589 | 0.4778 | 0.7691 |
| C304 | 0.0292 | 0.467 | 0.6798 |
| C305 | 0.9687 | 0.5474 | 0.7964 |
| N306 | 0.9393 | 0.537 | 0.7063 |
| H307 | 0.9371 | 0.4678 | 0.5421 |
| H308 | 0.9639 | 0.4374 | 0.5064 |
| H309 | 0.0608 | 0.5466 | 0.9342 |
| H310 | 0.034 | 0.5768 | 0.9702 |
| H311 | 0.0102 | 0.4384 | 0.5596 |
| H312 | 0.9875 | 0.5756 | 0.9175 |
| C313 | 0.9744 | 0.964 | 0.7467 |
| C314 | 0.0091 | −0.0175 | 0.764 |
| C315 | 0.0351 | −0.0264 | 0.7664 |
| C316 | 0.0283 | 0.0547 | 0.7503 |
| C317 | 0.9936 | 1.0362 | 0.7331 |
| C318 | 0.9678 | 0.9925 | 0.7322 |
| N319 | 0.0532 | 0.1285 | 0.7226 |

TABLE 6-continued

Fractional atomistic coordinates for crystal structure of TPAPC-COF.
TPAPC-COF
Space group: P1
a = 52.2892 Å, b = 40.7693 Å, c = 8.8687 Å
α = 95.604°, β = 104.523°, γ = 129.098°
$R_{wp}$ = 3.23%, $R_p$ = 2.27%

| Atom | a/x | b/y | c/z |
| --- | --- | --- | --- |
| C320 | 0.0573 | 0.1012 | 0.7517 |
| C321 | 0.9453 | 0.9173 | 0.7422 |
| N322 | 0.9472 | 0.887 | 0.7402 |
| H323 | 0.0158 | −0.0378 | 0.7759 |
| H324 | 0.0615 | 0.0391 | 0.7802 |
| H325 | 0.9869 | 1.0565 | 0.7206 |
| H326 | 0.9414 | 0.9798 | 0.7188 |
| H327 | 0.0835 | 0.1105 | 0.7759 |
| H328 | 0.9203 | 0.9095 | 0.7351 |
| C329 | 0.5336 | 0.5202 | 0.7459 |
| C330 | 0.5333 | 0.5545 | 0.7839 |
| C331 | 0.5025 | 0.5452 | 0.7838 |
| C332 | 0.4691 | 0.5013 | 0.7472 |
| C333 | 0.4694 | 0.467 | 0.7092 |
| C334 | 0.5002 | 0.4763 | 0.7087 |
| N335 | 0.4064 | 0.4587 | 0.7397 |
| C336 | 0.4374 | 0.4953 | 0.7514 |
| C337 | 0.5654 | 0.5264 | 0.7427 |
| N338 | 0.5977 | 0.564 | 0.7719 |
| H339 | 0.5578 | 0.5894 | 0.8147 |
| H340 | 0.5045 | 0.5735 | 0.8146 |
| H341 | 0.445 | 0.4321 | 0.6786 |
| H342 | 0.4982 | 0.4479 | 0.6778 |
| H343 | 0.4439 | 0.5276 | 0.7726 |
| H344 | 0.5584 | 0.4937 | 0.7133 |
| H345 | 0.1844 | 0.4254 | 0.6084 |
| H346 | 0.2241 | 0.4238 | 0.6613 |
| H347 | 0.3108 | 0.5909 | 0.3614 |
| H348 | 0.2696 | 0.5894 | 0.2651 |
| H349 | 0.8139 | 0.5904 | 0.8633 |
| H350 | 0.7727 | 0.589 | 0.767 |
| H351 | 0.6814 | 0.4261 | 0.1072 |
| H352 | 0.7211 | 0.4243 | 0.1605 |

TPAPC-COF affords the desymmetric structure with elliptical pores (FIG. 6B). As displayed in FIG. 6A, the experimental PXRD pattern shows four intense peaks at 2θ=3.35°, 3.86°, 6.15° and 7.02° for TPAPC-COF, along with other minor peaks, indicating long-range ordering in the framework. The possible extended structures were built by the Materials Studio suite of programs. The structural simulations suggested that TPAPC-COF preferably possesses the staggered AB stacking model (FIGS. 6B and 6C). In this model, Pawley refined profile matched well with the experimentally observed pattern, resulting in a good agreement factor ($R_{wp}$=3.23% and $R_p$=2.27%) and the reasonable profile difference (FIG. 6A). The refinement result yields unit cell parameters of a=52.2892 Å, b=40.7693 Å, c=8.8687 Å, α=95.604°, β=104.523°, and γ=129.098°. The AA eclipsed configuration for TPAPC-COF was also simulated, in which the calculated PXRD pattern mismatched the observed one (FIGS. 6A, 6D and 6E). The morphology of the activated TPAPC-COF samples was examined by scanning electron microscopy (SEM), which showed the aggregation of granular crystallites affording sphere-like morphology (FIG. 7A). High-resolution transmission electron microscopy (HRTEM) images revealed the clear crystal lattice of TPAPC-COF, which is reasonable for rr-rr stacking (FIG. 7B). The lattice fringe spacing of 0.31 nm can be measured from the HRTEM, and is close to the interlayer of TPAPC-COF.

Light-Absorption Properties of TPAPC-COF. To assess the light-absorption properties of TPAPC-COF, the electronic absorption spectra measurements were conducted. TPAPC-COF shows broad optical response covering the UV and entire visible spectral range, tailing far into the NIR region with an extended absorption to 2000 nm (FIG. 7D). It can be seen that TPAPC-COF exhibits an absorption band at 399 nm that is due to the Soret band, which is red-shifted by over 7 nm relative to that of the $H_3$TPAPC solid monomer. Particularly, compared to the observed Q-band peaks in the spectra of corrole monomer and its corresponding highly dilute solutions, the spectrum of TPAPC-COF displays a continuous absorption without a clear boundary between the Soret and Q-bands. At longer wavelengths the spectra of TPAPC-COF and corrole solid monomer are nearly identical. The optical bandgap, based on the absorption onset, is estimated to be 1.06 eV for TPAPC-COF.

Singlet Oxygen ($^1O_2$) Generation. In a typical experiment, 50 μg of the monomer or Corrole-COF materials was suspended in 1 mL of N-methylpyrrolidone (NMP) (equilibrated with air at RT) containing 10 μM of singlet oxygen sensor 1,3-diphenylisobenzofuran (DPBF). The mixture solutions were irradiated under a 635 nm laser (0.18 W cm$^{-2}$). The characteristic UV-Vis absorption spectra of the DPBF were measured at 415 nm to determine the generation of $^1O_2$ every 1 min, in which the UV-Vis absorption spectra of samples were collected using a UV-1800 spectrophotometer (Shimadzu, Japan) with a 0.3 cm quartz cuvette at room temperature.

TPAPC-COF was evaluated for its ability to generate $^1O_2$ (FIGS. 8A and 7B). The photo-generating $^1O_2$ ability of TPAPC-COF under a 635 nm laser (0.18 W/cm$^2$) irradiation was investigated by using 1,3-diphenylisobenzofuran (DPBF) as a scavenger, and the process was monitored by time-dependent electronic absorption spectroscopy. As displayed in FIG. 8C, irradiation of N-methylpyrrolidone (NMP) solutions (1.0 ml) containing DPBF (10 μM) in the presence of TPAPC-COF (50 μg) led to the steady generation of $^1O_2$, as evidenced by the spectral change of DPBF at λ=415 nm. It can be clearly observed from FIG. 8D that TPAPC-COF exhibited the strong ability to activate molecular oxygen with 90% degradation efficiency of DPBF, whereas the monomeric $H_3$TPAPC showed the sharply decreased activity for degrading DPBF with a low conversion of 56%, which indicate that the monomer system is much less active than TPAPC-COF.

Preparation of TPAPC-COF/DSPE-PEG2000 composite. The mixture solution of TPAPC-COF (2 mg/ml in $H_2O$) and DSPE-PEG2000 (1 mg/ml in $H_2O$) was stirred at room temperature for 24 h. Afterward, the resulting material was centrifuged and washed several times to remove the free DSPE-PEG2000, and further dried to obtain the composite material TPAPC-COF'.

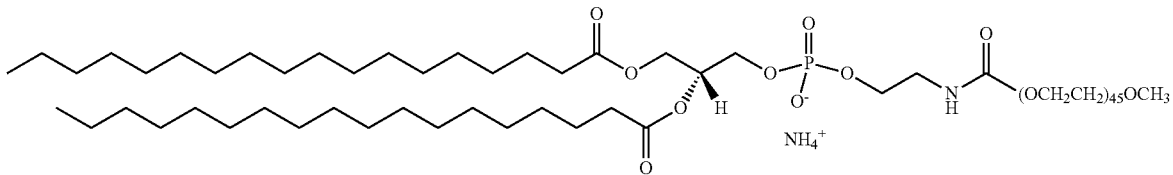

DSPE-PEG2000

Cell Cytotoxicity Assay of TPAPC-COF'. MCF-7 and NHDF cells ($5.0 \times 10^4$) were cultured for 12 h in a 96-well plate, and incubated for another 4 h using the fresh Opti-MEM alone or medium containing TPAPC-COF'. Then, the fresh medium replaced the Opti-MEM and incubated for 4 h. MTT (20 μL, 5 mg/mL) was then added to each well. The media was removed 4 h later, and sodium dodecylsulfate (DMSO, 100 μL) was added to solubilize the dye. After shocking (37° C., 120 rpm) for 15 min, the absorbance of each well was measured using Tecan Sunrise at 488 nm. The cytotoxicity of TPAPC-COF' was estimated by the percentage of growth inhibition calculated with the formula. Growth inhibition $\% = (1 - A_{text}/A_{control}) \times 100\%$. As shown in FIG. 9A, TPAPC-COF' exhibited no obvious toxicity for NHDF and MCF-7 cells even the concentration reaches 200 μg/ml, indicating its good biocompatibility.

Intracellular $^1O_2$ Generation. MCF-7 cells ($1.0 \times 10^4$) were cultivated on a confocal dish containing Dulbecco's modified Eagle's medium (DMEM, 1 ml) for 12 h. The medium was then replaced by fresh Opti-MEM containing TPAPC-COF' (50 μg/mL) and cultivated for 4 h. After washing each well twice using PBS (10 mM, pH=7.4), the fresh DMEM medium (1 ml) was added and cultured for another 8 h. The cells were irradiated with 635 nm laser (0.18 W cm$^{-2}$) for 5 min and cultured for 8 h. Intracellular $^1O_2$ was detected by means of Singlet Oxygen Sensor Green (SOSG) which could be oxidized to a highly fluorescent derivative, SOSG-Endoperoxide (SOSG-EP) in the presence of singlet oxygen. The SOSG-EP fluorescence was detected using a confocal laser scanning microscopy (CLSM, FV1200, Olympus, Japan). TPAPC-COF'-treated cells upon irradiation showed strong green fluorescence, whereas negligible fluorescent signal was detected in all the comparative groups, suggesting that TPAPC-COF' is capable of efficiently producing $^1O_2$ in MCF-7 cells (FIG. 9B).

In vitro Photodynamic Therapy. MCF-7 cells ($1.0 \times 10^5$) were cultivated on a confocal dish containing Dulbecco's modified Eagle's medium (DMEM, 1 ml) for 12 h. The medium was then replaced by fresh Opti-MEM alone as a control and fresh Opti-MEM containing TPAPC-COF' (50 μg/mL) and cultivated for 4 h. After washing each well twice using PBS (10 mM, pH=7.4), the fresh DMEM medium (1 ml) was added and cultured for another 8 h. The cells were irradiated with 635 nm laser (0.18 W cm$^{-2}$) for 10 min and cultured for 8 h. The activity of MCF-7 cells treated with TPAPC-COF' were measured by CLSM stained by Calcein AM and PI.

Compared to the experiments with different treatments of blank and laser or TPAPC-COF' alone, the activity of MCF-7 cells treated with TPAPC-COF' upon 635 nm laser irradiation is sharply decreased, and almost all of the cancer cells were damaged, indicating that TPAPC-COF' shows remarkable anticancer activity (FIG. 9C). These results demonstrate that corrole-COF served as a powerful photosensitizer material has promising potential for cancer therapy.

From the foregoing, it will be seen that aspects herein are well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings is to be interpreted as illustrative and not in a limiting sense.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A metal-organic framework, wherein the metal-organic framework comprises a structural unit comprising the formula II $$M_6(\mu_3-O)_4(\mu_3-OH)_4(OH)_3(H_2O)_3(TCPC)_9 \quad \text{II}$$

wherein M is Zr or Hf, and
TCPC is 5,10,15-tris(p-carboxylphenyl)corrole.

2. The metal-organic framework of claim 1, wherein the framework is a three dimensional (3,9)-connected gfy topology comprising hexagonal one dimensional open channels.

3. The metal-organic framework of claim 1, wherein the framework comprises hexagonal channels, wherein the pore size of the hexagonal channels is from about 20 Å to about 30 Å.

4. The metal-organic framework of claim 1, wherein the framework comprises channels along the a and b axis of the framework, wherein the channels have a width of from about 10 Å to about 20 Å.

5. The metal-organic framework of claim 1, wherein the framework further comprises a transition metal $M^1$, wherein the transition metal $M^1$ is coordinated by one or more pyrrole groups of the corrole moiety.

6. The metal-organic framework of claim 5, wherein the transition metal $M^1$ is different than M.

7. The metal-organic framework of claim 5, wherein the transition metal $M^1$ is the same as M.

8. The metal-organic framework of claim 5, wherein the transition metal $M^1$ is Fe(III) or Fe(IV).

9. An organic framework produced by reacting 5,10,15-tris(p-aminophenyl)corrole ($H_3$TPAPC) with a compound of formula III

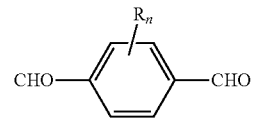

wherein R is hydrogen, an alkyl group, aryl group, an aralkyl group, a halide group, a cyano group, a hydroxy group, alkoxy group, a carboxyl group, or a nitro group, or a fused aryl group, and n is an integer from 1 to 4.

10. The organic framework of claim 9, wherein R is hydrogen and n is 4.

11. The organic framework of claim 9, wherein the molar ratio of the compound of formula III to 5, 10, 15-tris(p-aminophenyl)corrole is from about 1:1 to about 2:1.

12. A method for conducting a Diels-Alder reaction, comprising reacting a diene and dienophile in the presence of the metal-organic framework according to claim 1.

13. A method for damaging cancer cells, the method comprising irradiating the cancer cells in the presence of the organic framework according to claim 1.

14. A method for treating cancer in a subject, the method comprising (1) administering the organic framework according to claim 1 to the subject and (2) irradiating the organic framework.

15. A method for generating singlet oxygen, the method comprising irradiating the organic framework according to claim 1.

* * * * *